US006306876B1

(12) United States Patent
Carson et al.

(10) Patent No.: US 6,306,876 B1
(45) Date of Patent: Oct. 23, 2001

(54) 4-[ARYL(8-AZABICYCLO[3.2.1]OCTAN-3-YL)] AMINOBENZOIC ACID DERIVATIVES

(75) Inventors: John R. Carson, Norristown; Robert E. Boyd, Horsham; Lou Anne Neilson, Sellersville, all of PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/728,972

(22) Filed: Dec. 4, 2000

Related U.S. Application Data

(60) Provisional application No. 60/171,422, filed on Dec. 22, 1999.

(51) Int. Cl.[7] .......................... A61K 31/46; C07D 451/04
(52) U.S. Cl. ...................... 514/304; 514/233.2; 514/253; 514/256; 544/127; 544/335; 544/362; 546/124; 546/125; 546/126
(58) Field of Search ..................................... 546/124, 125, 546/126; 544/127, 335, 362; 514/233.2, 253, 256, 304

(56) References Cited

FOREIGN PATENT DOCUMENTS

| | | |
|---|---|---|
| WO93/15062 A1 | 8/1993 | (WO) . |
| WO97/23466 A1 | 7/1997 | (WO) . |
| WO98/28270 A1 | 7/1998 | (WO) . |
| WO98/28275 A1 | 7/1998 | (WO) . |
| WO99/33806 A1 | 8/1999 | (WO) . |
| 00/33055 | 4/2000 | (WO) . |

OTHER PUBLICATIONS

Thomas J. B. et al.; "Optically Pure (–)–4–[(N–Allyl–3–Methyl–4–Piperidinyl) Phenylamino]–N, N–Diethylbenzamide Displays Selective Binding and Full Agonist Activity for the delta Opioid Receptor"; Bioorganic & Medical Chemistry Letters, GB, Oxford, vol. 9, No. 23, Dec. 6, 1999 (Dec. 6, 1999), pp. 3347–3350.

Thomas J. B. et al.; "(+–)–4' (N–A (N–Allyl–3–Methyl–4–Piperidinyl) Phenylamino!–N, N–Diethylbenzami de Displays Selective Binding for the Delta Opioid Receptor"; Bioorganic & Medical Chemistry Letters, GB, Oxford, vol. 9, No. 20, Oct. 18, 1999 (Oct. 18, 1999), pp. 3053–3056.

Jerome R Bagley and Thomas N. Riley, Synthesis and Conformational Analysis of Isomeric 3–Propananilidotropanes, J. heterocyclic Chem., 14, 599(1977).

Bozenna Gutkowska, Jacek Stefanowicz, Zdzislawa Stefanowicz, Syntezy Niektorych Amidow Pochodnych 3–Aminotropanu O Spodziewanym Dzialaniu Farmakologicznym. I. Acta Polon, Pharm, XLI, NR 6, 1984.

*Primary Examiner*—Bernard Dentz
(74) *Attorney, Agent, or Firm*—John Harbour

(57) ABSTRACT

4-[aryl(8-azabicyclo[3.2.1]octan-3yl)]aminobenzoic acid derivatives are delta-opioid receptor modulators. As delta-opioid receptor agonists, such compounds are useful as analgesics. Depending on their antagonist effect, such compounds may also be useful immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases.

30 Claims, No Drawings

4-[ARYL(8-AZABICYCLO[3.2.1]OCTAN-3-YL)] AMINOBENZOIC ACID DERIVATIVES

This application is accorded the benefit of Verified Provisional Application 60/171,422 which was filed Dec. 22, 1999.

FIELD OF THE INVENTION

The present invention is directed to delta-opioid receptor modulators. More particularly, the present invention is directed to 4-[aryl(8-azabicyclo[3.2.1]octan-3-yl)] aminobenzoic acid derivatives which are delta-opioid receptor modulators useful as effective analgesics.

BACKGROUND OF THE INVENTION

WO 97/23466 discloses compounds described as having an analgesic effect, having a general and a typical preferred formula:

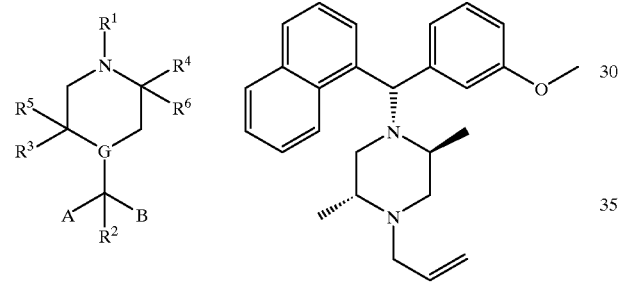

WO 98/28270 also discloses compounds described as having an analgesic effect, having a general and a typical preferred formula:

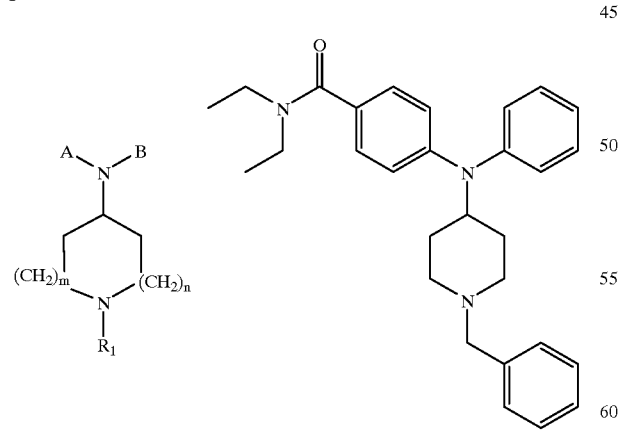

WO 98/28275 further discloses compounds described as having an analgesic effect, having a general and a typical preferred formula:

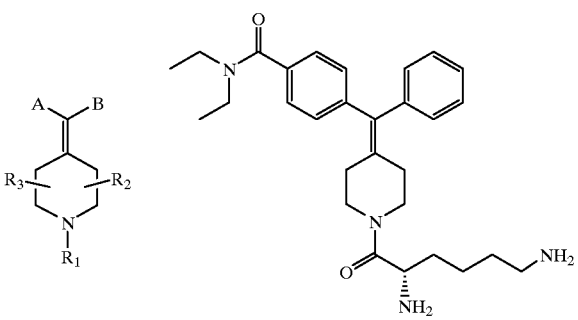

Isomeric 3-propananilidotropane are used as intermediates herein and have been published in Bagley, J. R., et al., J. Heterocycl. Chem., 1977, 14(4), 599–602, having the following formulae:

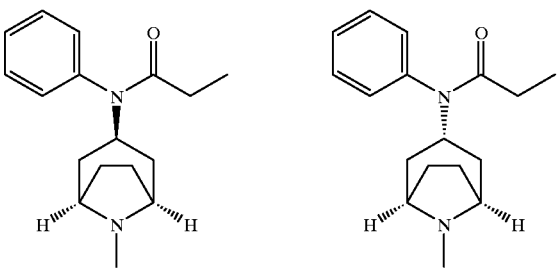

Amide derivatives of 3-aminotropane are also used as intermediates herein and have been prepared and described as having potential pharmacological activity, Gutkowska, B., et al., Acta Pol. Pharm., 1984, 41(6), 613–617, having the formula:

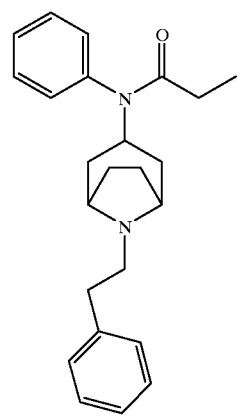

WO 93/15062 discloses compounds which have been described as delta-opioid and mu-opioid receptor agonists, having (approximately) the formula:

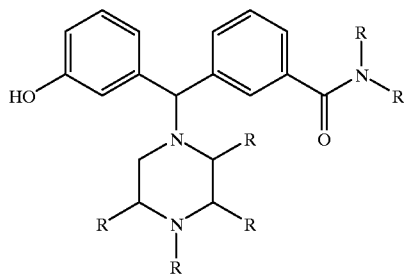

The foregoing reference compounds have been described as either delta- or mu-opioid receptor agonists or antagonists.

It is an object of the present invention to provide delta-opioid receptor modulators. It is another object of the present invention to provide delta-opioid receptor selective agonists as analgesics having reduced side-effects. It is also another object of the present invention to provide delta-opioid receptor antagonists as immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases, having reduced side-effects. It is a further object of the present invention to provide a method for treating a disorder modulated by the delta-opioid receptor.

SUMMARY OF THE INVENTION

There are provided by the present invention delta-opioid receptor modulators of Formula (I):

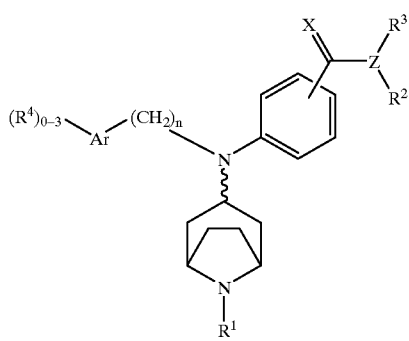

Formula (I)

wherein:

R$^1$ is a substituent selected from the group consisting of hydrogen, (C$_{1-8}$)alkyl, (C$_{2-6}$)alkenyl, (C$_{3-7}$)cycloalkyl, (C$_{3-6}$)cycloalkyl(C$_{1-3}$)alkyl, (C$_{1-6}$)alkoxy(C$_{1-3}$)alkyl, 4-(C$_{1-4}$)alkyl-4,5-dihydro-5-oxo-1H-tetrazol-1-yl(C$_{1-4}$) alkyl, 2-thienyl(C$_{1-4}$)alkyl, 3-thienyl(C$_{1-4}$)alkyl, 2-furanyl(C$_{1-4}$)alkyl, 3-furanyl(C$_{1-4}$)alkyl, 2-pyrrolyl (C$_{1-4}$)alkyl, 3-pyrrolyl(C$_{1-4}$)alkyl, 2-pyridinyl(C$_{1-4}$) alkyl, 3-pyridinyl(C$_{1-4}$)alkyl, 4-pyridinyl(C$_{1-4}$)alkyl, 3-pyrazolyl(C$_{1-4}$)alkyl, 4-pyrazolyl(C$_{1-4}$)alkyl, 5-pyrazolyl(C$_{1-4}$)alkyl, 2-pyrimidinyl(C$_{1-4}$)alkyl, 4-pyrimidinyl(C$_{1-4}$)alkyl, 5-pyrimidinyl(C$_{1-4}$)alkyl, 6-pyrimidinyl(C$_{1-4}$)alkyl, 2-thiazolyl(C$_{1-4}$)alkyl, 4-thiazolyl(C$_{1-4}$)alkyl, 5-thiazolyl(C$_{1-4}$)alkyl, 2-oxazolyl(C$_{1-4}$)alkyl, 4-oxazolyl(C$_{1-4}$)alkyl, 5-oxazolyl(C$_{1-4}$)alkyl, phenyl(C$_{1-4}$)alkyl and phenyl (C$_{2-4}$)alkenyl; wherein the foregoing thienyl, furanyl, pyrrolyl, thiazolyl, oxazolyl, pyrazolyl, pyridinyl, pyrimidinyl and phenyl substituents are optionally substituted with one to three substituents independently selected from the group consisting of hydroxy, halogen, (C$_{1-3}$)alkyl, (C$_{2-3}$)alkenyl, (C$_{1-3}$)alkoxy, (C$_{1-3}$)acyl, (C$_{1-10}$)acyloxy, cyano, amino, (C$_{1-3}$)acylamino, (C$_{1-3}$) alkylamino, di(C$_{1-3}$)alkylamino, (C$_{1-3}$)alkylthio, (C$_{1-3}$) alkylsulfonyl, —OCH$_2$O—, —O(CH$_2$)$_2$O—, trifluoromethyl and trifluoromethoxy;

R$^2$ and R$^3$ are independently selected from the group consisting of hydrogen, (C$_{1-8}$)alkyl (optionally substituted with one to three halogen substituents), (C$_{2-6}$) alkenyl, (C$_{3-7}$)cycloalkyl, phenyl (wherein phenyl is optionally substituted with one to three substituents independently selected from the group consisting of halogen, (C$_{1-6}$)alkyl, (C$_{2-6}$)alkenyl, (C$_{3-7}$)cycloalkyl, —OCH$_2$O—, —O(CH$_2$)$_2$O— and trifluoromethyl), benzyl (wherein benzyl is optionally substituted with one to three substituents independently selected from the group consisting of halogen, (C$_{1-6}$)alkyl, (C$_{2-6}$) alkenyl, (C$_{1-6}$)alkoxy, (C$_{3-7}$)cycloalkyl, —OCH$_2$O—, —O(CH$_2$)$_2$O— and trifluoromethyl), hydroxy(C$_{1-4}$) alkyl, (C$_{1-6}$)alkoxy(C$_{1-4}$)alkyl and trifluoro(C$_{1-4}$) alkoxy; alternatively, R$^2$ and R$^3$ may form a single fused moiety selected from the group consisting of 1,4-butylene, 1,5-pentylene, 1,5-(3-oxapentylene) and 1,5-(3-azapentylene); wherein the moiety is optionally substituted with one to four substituents independently selected from the group consisting of (C$_{1-6}$)alkyl, (C$_{2-6}$) alkenyl and (C$_{3-7}$)cycloalkyl;

the moiety —C(=X)Z is substituted on phenyl at the 3 or 4 position; wherein X is selected from the group consisting of S and O; Z is selected from the group consisting of N and O; and, Z is optionally substituted with one to two substituents independently selected from the group consisting of R$^2$ and R$^3$;

with the proviso that:

if Z is O, then Z is optionally substituted with one substituent selected from R$^2$;

n is selected from 0 or 1;

Ar is selected from the group consisting of phenyl, 1-naphthyl and 2-naphthyl; wherein Ar is optionally substituted with from one to three substituents independently selected from R$^4$;

R$^4$ is independently selected from the group consisting of hydroxy, halogen, (C$_{1-3}$)alkyl, (C$_{2-3}$)alkenyl, (C$_{1-3}$) alkoxy, (C$_{1-3}$)acyl, (C$_{1-10}$)acyloxy, cyano, amino, (C$_{1-3}$)acylamino, (C$_{1-3}$)alkylamino, di(C$_{1-3}$) alkylamino, (C$_{1-3}$)alkylthio, (C$_{1-3}$)alkylsulfonyl, —OCH$_2$O—, —O(CH$_2$)$_2$O—, trifluoromethyl and trifluoromethoxy; and, alternatively, two adjacent R$^4$ groups may form a single fused moiety, wherein the moiety is selected from the group consisting of —(CH$_2$)$_{3-5}$— and —O(CH$_2$)$_{1-3}$O—;

and pharmaceutically acceptable diastereomers and salts thereof.

DETAILED DESCRIPTION OF THE INVENTION

Embodiments of a compound of Formula (I) include those compounds wherein, preferably, R$^1$ is selected from the group consisting of hydrogen, methyl, ethyl, n-propyl, n-butyl, 2-ethyl-n-butyl, n-hexyl, cyclopropylmethyl, cyclohexylmethyl, cyclohexyl, allyl, 3,3-dimethylallyl, 2-methylpropenyl, piperonyl, phenethyl, 4-fluorophenethyl, 3,4-dimethoxyphenethyl, diphenylethyl, phenylpropyl, 2-thienylethyl and 2-furanylmethyl. More preferably, $R^1$ is selected from the group consisting of hydrogen, methyl, n-propyl, allyl, piperonyl, 3,4-dimethoxyphenethyl, phenyl-propyl and 2-furanylmethyl. Most preferably, $R^1$ is selected from the group consisting of hydrogen, allyl and piperonyl.

Embodiments of a compound of Formula (I) also include those compounds wherein, preferably, $R^2$ and $R^3$ are independently selected from the group consisting of methyl, ethyl, 2-fluoroethyl, n-propyl, isopropyl, n-butyl, t-butyl, 2-methylallyl, phenyl, 3-fluorophenyl and 4-methylbenzyl; and, alternatively, $R^2$ and $R^3$ may form a single fused moiety selected from 1,4-butylene. More preferably, $R^2$ and $R^3$ are independently selected from the group consisting of methyl, ethyl, 2-fluoroethyl, n-propyl, n-butyl, 2-methylallyl, phenyl and 3-fluorophenyl. Most preferably, $R^2$ and $R^3$ are independently selected from ethyl.

Embodiments of a compound of Formula (I) further include those compounds wherein, preferably, n is 0.

An embodiment of a compound of Formula (I) includes those compounds wherein, preferably, Ar is phenyl.

An embodiment of a compound of Formula (I) also includes those compounds wherein, preferably, $R^4$ is independently selected from the group consisting of hydroxy, chloro, bromo, fluoro, methyl, ethyl, methoxy, ethoxy, methylamino, N,N-dimethylamino, methylthio, methylsulfonyl, trifluoromethoxy and trifluoromethyl. More preferably, $R^4$ is independently selected from the group consisting of hydroxy, methoxy and methylthio. Most preferably, $R^4$ is not present.

Exemplified compounds of the present invention are listed in Table 1 and have the general structure:

Table 1

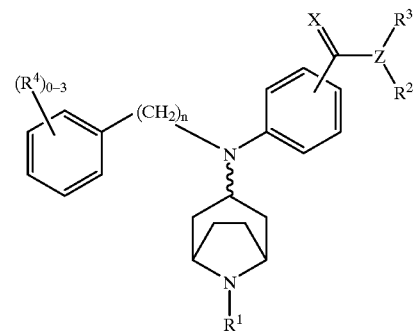

wherein $R^1$, —C(=X)Z, $R^2$, $R^3$, n and $R^4$ are dependently selected from the group consisting of:

| Ex # | $R^1$ | —C(=X)Z | $R^2$ | $R^3$ | n | $R^4$ |
|---|---|---|---|---|---|---|
| $1_{endo}$ | $CH_3$ | 4-C(=O)N | $CH_2CH_3$ | $CH_2CH_3$ | 0 | ---; |
| $2_{endo}$ | $CH_3$ | 4-C(=O)N | $CH_2CH_3$ | $CH_2CH_3$ | 0 | 3-$OCH_3$; |
| $3_{endo}$ | $CH_3$ | 4-C(=O)N | $CH_2CH_3$ | $CH_2CH_3$ | 0 | 3-$SCH_3$; |
| $4_{endo}$ | $CH_3$ | 4-C(=O)N | $CH_2CH_3$ | $CH_2CH_3$ | 1 | ---; |
| $5_{endo}$ | H | 4-C(=O)N | $CH_2CH_3$ | $CH_2CH_3$ | 0 | ---; |
| $6_{endo}$ | $(CH_2)_2Ph$ | 4-C(=O)N | $CH_2CH_3$ | $CH_2CH_3$ | 0 | ---; |
| $7_{endo}$ | $(CH_2)_2CH_3$ | 4-C(=O)N | $CH_2CH_3$ | $CH_2CH_3$ | 0 | ---; |
| $8_{endo}$ | $C_6H_{11}$ | 4-C(=O)N | $CH_2CH_3$ | $CH_2CH_3$ | 0 | ---; |
| $9_{endo}$ | piperonyl | 4-C(=O)N | $CH_2CH_3$ | $CH_2CH_3$ | 0 | ---; |
| $10_{endo}$ | $CH_2CH=CH_2$ | 4-C(=O)N | $CH_2CH_3$ | $CH_2CH_3$ | 0 | ---; |
| $11_{exo}$ | $CH_3$ | 4-C(=O)N | $CH_2CH_3$ | $CH_2CH_3$ | 0 | ---; |
| $12_{exo}$ | $CH_3$ | 4-C(=O)N | $(CH_2)_2CH_3$ | $(CH_2)_2CH_3$ | 0 | ---; |
| $13_{exo}$ | H | 4-C(=O)N | $CH_2CH_3$ | $CH_2CH_3$ | 0 | ---; |
| $14_{exo}$ | $CH_3$ | 4-C(=O)N | H | $(CH_2)_2CH_3$ | 0 | ---; |
| $15_{exo}$ | $(CH_2)_5CH_3$ | 4-C(=O)N | $CH_2CH_3$ | $CH_2CH_3$ | 0 | ---; |
| $16_{exo}$ | $(CH_2)_2CH_3$ | 4-C(=O)N | $CH_2CH_3$ | $CH_2CH_3$ | 0 | ---; |
| $17_{exo}$ | $(CH_2)_2Ph$ | 4-C(=O)N | $CH_2CH_3$ | $CH_2CH_3$ | 0 | ---; |
| $18_{exo}$ | $CH_2CH(Ph)_2$ | 4-C(=O)N | $CH_2CH_3$ | $CH_2CH_3$ | 0 | ---; |
| $19_{exo}$ | $CH_2C_6H_{11}$ | 4-C(=O)N | $CH_2CH_3$ | $CH_2CH_3$ | 0 | ---; |
| $20_{exo}$ | $CH_2CH(CH_2CH_3)_2$ | 4-C(=O)N | $CH_2CH_3$ | $CH_2CH_3$ | 0 | ---; |
| $21_{exo}$ | 2-furanyl$CH_2$ | 4-C(=O)N | $CH_2CH_3$ | $CH_2CH_3$ | 0 | ---; |
| $22_{exo}$ | piperonyl | 4-C(=O)N | $CH_2CH_3$ | $CH_2CH_3$ | 0 | -.--; |
| $23_{exo}$ | $CH_2CH=C(CH_3)_2$ | 4-C(=O)N | $CH_2CH_3$ | $CH_2CH_3$ | 0 | ---; |
| $24_{exo}$ | $(CH_2)_2$-3,4-$(CH_3O)_2Ph$ | 4-C(=O)N | $CH_2CH_3$ | $CH_2CH_3$ | 0 | ---; |
| $25_{exo}$ | $(CH_2)_2$-F-Ph | 4-C(=O)N | $CH_2CH_3$ | $CH_2CH_3$ | 0 | ---; |
| $26_{exo}$ | $(CH_2)_3Ph$ | 4-C(=O)N | $CH_2CH_3$ | $CH_2CH_3$ | 0 | ---; |
| $27_{exo}$ | $(CH_2)_2Ph$ | 4-C(=O)N | $(CH_2)_2CH_3$ | $(CH_2)_2CH_3$ | 0 | ---; |
| $28_{endo}$ | $CH_3$ | 4-C(=O)O | $C(CH_3)_3$ | — | 0 | ---; |
| $29_{endo}$ | $CH_3$ | 4-C(=O)O | — | — | 0 | ---; |
| $30_{endo}$ | $CH_3$ | 4-C(=O)N | $CH_3$ | $CH_3$ | 0 | ---; |
| $31_{endo}$ | $CH_3$ | 4-C(=O)N | —$(CH_2)_4$— | | 0 | ---; |
| $32_{endo}$ | $CH_3$ | 4-C(=O)N | $CH_3$ | $CH_2CH_3$ | 0 | ---; |
| $33_{endo}$ | $CH_3$ | 4-C(=O)N | $CH_2CH_3$ | $CH_2C(CH_3)=CH_2$ | 0 | ---; |
| $34_{endo}$ | $CH_3$ | 4-C(=O)N | $CH_2CH_3$ | $CH_2(4-CH_3Ph)$ | 0 | ---; |
| $35_{endo}$ | $CH_3$ | 4-C(=O)N | $(CH_2)_2CH_3$ | $(CH_2)_3CH_3$ | 0 | ---; |
| $36_{endo}$ | $CH_3$ | 4-C(=O)N | $CH_3$ | Ph | 0 | ---; |
| $37_{endo}$ | $CH_3$ | 4-C(=O)N | $(CH_2)_2CH_3$ | $(CH_2)_2CH_3$ | 0 | ---; |
| $38_{endo}$ | $CH_3$ | 3-C(=O)O | $C(CH_3)_3$ | — | 0 | ---; |
| $39_{endo}$ | $CH_3$ | 4-C(=O)N | — | H | 0 | ---; |
| $40_{endo}$ | $CH_3$ | 3-C(=O)N | $CH_2CH_3$ | $CH_2CH_3$ | 0 | ---; |
| $41_{endo}$ | $(CH_2)_2Ph$ | 4-C(=O)O | $C(CH_3)_3$ | — | 0 | ---; |

-continued

| Ex # | R$^1$ | —C(=X)Z | R$^2$ | R$^3$ | n | R$^4$ |
|---|---|---|---|---|---|---|
| 42$_{endo}$ | (CH$_2$)$_2$Ph | 4-C(=O)O | — | — | 0 | ---; |
| 43$_{endo}$ | (CH$_2$)$_2$Ph | 4-C(=O)N | CH$_3$ | CH$_3$ | 0 | ---; |
| 44$_{endo}$ | (CH$_2$)$_2$Ph | 4-C(=O)N | CH$_3$ | CH$_2$CH$_3$ | 0 | ---; |
| 45$_{endo}$ | (CH$_2$)$_2$Ph | 4-C(=O)N | CH$_2$CH$_3$ | (CH$_2$)$_3$CH$_3$ | 0 | ---; |
| 46$_{endo}$ | (CH$_2$)$_2$Ph | 4-C(=O)N | (CH$_2$)$_2$CH$_3$ | (CH$_2$)$_2$CH$_3$ | 0 | ---; |
| 47$_{endo}$ | (CH$_2$)$_2$Ph | 4-C(=O)N | CH$_3$ | (CH$_2$)$_2$CH$_3$ | 0 | ---; |
| 48$_{endo}$ | (CH$_2$)$_2$Ph | 4-C(=O)N | CH$_3$ | (CH$_2$)$_3$CH$_3$ | 0 | ---; |
| 49$_{endo}$ | (CH$_2$)$_2$Ph | 4-C(=O)N | CH$_2$CH$_3$ | CH$_2$C(CH$_3$)=CH$_2$ | 0 | ---; |
| 50$_{endo}$ | (CH$_2$)$_2$Ph | 4-C(=O)N | —(CH$_2$)$_4$— | | 0 | ---; |
| 51$_{endo}$ | CH$_3$ | 4-C(=S)N | CH$_2$CH$_3$ | CH$_2$CH$_3$ | 0 | ---; |
| 52$_{endo}$ | H | 3-C(=O)N | CH$_3$ | 3-F-Ph | 0 | 3-OCH$_3$; |
| 53$_{endo}$ and, | CH$_2$CH=CH$_2$ | 3-C(=O)N | CH$_3$ | 3-F-Ph | 0 | 3-OCH$_3$; |
| 54$_{endo}$ | CH$_2$CH=CH$_2$ | 3-C(=O)N | CH$_3$ | 3-F-Ph | 0 | 3-OH; | and pharmaceutically acceptable diastereomers and salts thereof.

The compounds of the present invention may also be present in the form of a pharmaceutically acceptable salt. The pharmaceutically acceptable salt generally takes a form in which the basic nitrogen is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharic or trifluoroacetic.

Where the compounds according to this invention have at least one chiral center, they may accordingly exist as enantiomers. In addition, where the compounds possess two or more chiral centers, they may additionally exist as diastereomers. In the present invention, for example, endo diastereomers are those with the diphenylamino group on the same side of the piperidine ring as the two carbon bridge. Exo diastereomers are those with the diphenylamino group on the opposite side of the piperidine ring as the two carbon bridge. It is to be understood that all such enantiomers and diastereomers, as well as all mixtures thereof, are encompassed within the scope of the present invention.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The terms used in describing the invention are commonly used and known to those skilled in the art. However, the terms that could have other meanings are hereinafter defined. These definitions apply to the terms as they are used throughout this specification, unless otherwise limited in specific instances, either individually or as part of a larger group.

An "independently" selected substituent refers to a group of substituents, wherein the substituents may be different. Therefore, designated numbers of carbon atoms (e.g., $C_1$–$C_8$) shall refer independently to the number of carbon atoms in an alkyl or cycloalkyl moiety or to the alkyl portion of a larger substituent in which alkyl appears as its prefix root.

The term "alkyl" refers to straight and branched-chain alkyl radical groups and the term "alkylene" refers to a corresponding straight and branched-chain alkyl linking group. Similarly, the "alkenyl" and "alkynyl" refers to radical groups having straight and branched chains with 2 to 8 carbon atoms or any number within this range, wherein one or two double bonds or one triple bond is formed in the chain between adjacent members. The term "alkoxy" refers to O-alkyl groups where alkyl is as defined supra. The term cycloalkyl refers to a cyclic alkyl ring of five to seven carbon atom members. Examples of such cyclic alkyl rings include pentyl, hexyl or heptyl.

The term aryl refers to a single aromatic ring of six carbon members or a bicyclic aromatic ring of ten carbon members. Examples of such aryl rings include phenyl and naphthyl.

The term heteroaryl refers to an aromatic ring of five or six members wherein the ring has at least one heteroatom member. Suitable heteroatoms include nitrogen, oxygen or sulfur. In the case of five-membered rings, the heteroaryl ring contains one member of nitrogen, oxygen or sulfur and, in addition, may contain up to two additional nitrogens. In the case of six-membered rings, the heteroaryl ring may contain from one to three nitrogen atoms. For the case wherein the six member ring has three nitrogens, at most two nitrogen atoms are adjacent.

The terms "$C_{1-6}$alkoxy($C_{1-6}$)alkyl," "$C_{3-6}$cycloalkyl($C_{1-3}$)alkyl" or "hydroxy($C_{1-6}$)alkyl" refer to an alkylene group substituted at the terminal carbon with an alkoxy, cycloalkyl or hydroxy group, respectively. Similarly, the term "phenyl($C_{2-4}$)alkenyl," refers to an alkenylene group substituted at the terminal carbon with a phenyl. The term "$C_{1-6}$ alkoxycarbonyl refers to a carbonyl linking group substituted with a terminal alkoxy group. The term "carbonyl" refers to the linking group —C=O—. Furthermore, the term "methylenedioxy" refers to the substituent moiety —OCH$_2$O— and the term "ethylenedioxy" refers to the substituent moiety —O(CH$_2$)$_2$O—.

Whenever the term "alkyl" appears in the name of a substituent (e.g., hydroxy($C_{1-6}$)alkyl) it shall be interpreted as including those limitations given above for "alkyl." Designated numbers of carbon atoms (e.g., $C_{1-6}$) shall refer independently to the number of carbon atoms in an alkyl or cycloalkyl moiety or to the alkyl portion of a larger substituent in which alkyl appears as its prefix root.

The term "hydroxy" or "oxy" refers to the group —OH and the term "oxo" refers to the group=O.

The term "halogen" shall include iodine, bromine, chlorine and fluorine.

Exemplary substituents include one or more alkyl groups as described above or one or more groups described above as substituted alkyl.

The novel compounds of Formula (I) are useful delta-opioid receptor modulators. In particular, the instant compounds are delta-opioid receptor selective agonists useful as analgesics having reduced side-effects. Examples of pain intended to be within the scope of the present invention include, but are not limited to, centrally mediated pain, peripherally mediated pain, structural or soft tissue injury related pain, progressive disease related pain, neuropathic pain and acute pain such as caused by acute injury, trauma or surgery and chronic pain such as caused by neuropathic conditions, diabetic peripheral neuropathy, post-herpetic neuralgia, trigeminal neuralgia, post-stroke pain syndromes or cluster or migraine headaches. The utility of the instant compounds as delta-opioid receptor selective agonists can be determined according to the procedures described herein.

Also, the compounds of the present invention are delta-opioid receptor selective antagonists useful as immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases, having reduced side-effects. The utility of the instant compounds as delta-opioid receptor selective antagonists can be determined by those skilled in the art using established animal models.

An embodiment of the invention is a pharmaceutical composition comprising one or more compounds of this invention in association with a pharmaceutically acceptable carrier. Another embodiment is a pharmaceutical composition made by mixing any of the compounds described above and a pharmaceutically acceptable carrier. A further embodiment is a process for making a pharmaceutical composition comprising mixing any of the compounds described above and a pharmaceutically acceptable carrier.

To prepare the pharmaceutical compositions of this invention, one or more compounds of the invention or salt thereof, as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The present invention is also embodied by a pharmaceutical composition comprising a combination of a delta-opioid receptor modulator compound of the present invention and a mu-opioid receptor modulator compound having a synergistic analgesic effect. The utility of the instant combination product can be determined by those skilled in the art using established animal models.

Suitable mu-opioid receptor modulator compounds for use in such a combination include, without limitation, the compounds alfentanil, allylprodine, alphaprodine, anileridine, benzyl-morphine, bezitrarnide, buprenorphine, butorphanol, clonitazene, cyclazocine, desomorphirie, dextromoramide, dezocine, diampromide, diamorphone, dihydrocodeine, dihydromorphine, dimenoxadol, dimepheptanol dimethylthiambutene, dioxaphetylbutyrate, dipipanone, eptazocine, ethoheptazine, ethylmethylthiambutene, ethylmorphine, etonitazene, fentanyl, heroin, hydrornorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, diastereomers thereof, salts thereof, complexes thereof; and mixtures of any of the foregoing.

The present invention includes a method for treating a disorder modulated by the delta-opioid receptor. An embodiment of the present invention is a method for treating pain modulated by a delta-opioid agonist. Another embodiment is a method for treating immune disorders, inflammation, neurological conditions, psychiatric conditions, drug abuse, alcohol abuse, gastritis, diarrhea, cardiovascular disorders or respiratory disorders modulated by a delta-opioid antagonist.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The present invention therefore provides a method for the use of the instant compounds as delta-opioid receptor modulators in a subject in need thereof which comprises administering any of the compounds as defined herein in a therapeutically effective dose to modulate the delta-opioid receptor. A compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

A therapeutically effective dose for use of the instant compounds or a pharmaceutical composition thereof as a delta-opioid receptor selective agonist, delta-opioid receptor selective antagonist or in a combination delta-opioid/mu-opioid receptor modulator product comprises a dose range of from about 0.01 mg to about 12,000 mg, in particular from about 0.1 mg to about 4000 mg or, more particularly from about 1 mg to about 2000 mg of active ingredient per day for an average (70 kg) human.

For oral administration, a pharmaceutical composition is preferably provided in the form of tablets containing, 0.01, 0.05, 0.1, 0.5,1.0, 2.5, 5.0, 10.0, 15.0, 25.0, 50.0, 100, 150, 200, 250 and 500 milligrams of the active ingredient for the symptomatic adjustment of the dosage to the subject to be treated. Advantageously, compounds of the present invention may be administered in a single daily dose or the total daily dosage may be administered in divided doses of two, three or four times daily.

It is apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Compounds of this invention may be administered in any of the foregoing compositions and dosage regimens or by means of those compositions and dosage regimens established in the art whenever use of the compounds of the invention as delta-opioid receptor modulators is required for a subject in need thereof.

The terms used in describing the invention are commonly used and known to those skilled in the art. As used herein, the following abbreviations have the indicated meanings:

| | |
|---|---|
| BINAP | 2,2'-Bis(diphenylphosphino)-1,1'-binaphthyl |
| DCE | 1,2-dichloroethane |
| Et$_2$O | Diethyl ether |
| EtOH | Ethanol |
| h | Hour |
| HATU | O-(7-azabenzotriazol-1-yl)-N,N,N',N'-tetramethyluronium hexafluorophosphate |
| HBTU | 2-(1H-benzotriazole-1-yl)-1,1,3,3-tertamethyluronium hexafluorophosphate |
| K$_2$CO$_3$ | Potassium carbonate |
| MeCN | Methyl cyanide |
| MeOH | Methanol |
| NaBH$_4$ | Sodium borohydride |
| Na(OAc)$_3$BH | Sodium triacetoxyborohydride |
| NaOt-Bu | Sodium tert-butoxide |
| min | Minute |
| 2-prOH | 2-propanol |
| Pd$_2$dba$_3$ | Tris(dibenzylideneacetone)-dipalladium(0) |
| rt | room temperature |
| Ti(i-PrO)$_4$ | Titanium(IV) isopropoxide |

General Synthetic Methods

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

In general, 3-diarylamino-8-substituted-8-azabicyclo [3:2:1]octanes and 3-(N-aryl-N-benzyl)amino-8-substituted-8-azabicyclo[3:2:1]octanes bearing a carboxylic acid derivative on an aryl ring were prepared using synthetic methods wherein an 8-substituted-8-azabicyclo[3:2:1]octan-3-one compound was caused to reductively alkylate an aniline or a benzylamine compound.

As shown in Scheme 1, 2 and 3, for example, the 8-substituted-8-azabicyclo[3:2:1]octan-3-one Compound 1a, 2a and 3a was 8-methyl-8-azabicyclo[3:2:1]octan-3-one. Alternatively, as shown in Scheme 4 and 5, the 8-substituted-8-azabicyclo[3:2:1]octan-3-one Compound 4a and 5a used has a variable R$^1$ group.

Scheme 1, 3, 4 and 5 illustrate the reductive alkylation of the aniline Compound 1b, 3b, 4b and 5b using a 8-substituted-8-azabicyclo[3:2:1]octan-3-one Compound 1a, 3a, 4a and 5a, respectively.

Scheme 2 illustrates the reductive alkylation of the benzylamine Compound 2b using a 8-substituted-8-azabicyclo[3:2:1]octan-3-one Compound 2a.

The reducing agent employed determined the stereochemistry of the amine Compounds 1c, 2c, 3c, 4c and 5c produced. Hydride reducing agents or catalytic reduction produced the endo isomers. Sodium in ethanol afforded mixtures of exo and endo isomers which were then separated. The amine compounds thus produced were then arylated by reaction with an aryl halide bearing a carboxylic acid derivative while using a palladium catalyst to produce the target compounds of the synthesis. The particular R$^1$, —C(=X)Z, R$^2$ and R$^3$ functions desired in the target Compounds 1f, 2d, 3f, 4f and 5f may be incorporated into the original starting materials or may be added in later steps. For example, the synthetic sequence may be carried out starting with 8-azabicyclo[3:2:1]octanone bearing a removable R$^1$ group such as t-butoxycarbonyl (Boc) or CBz on the 8-position. At the conclusion of the sequence, the blocking group may be removed and replaced with the desired R$^1$ substituent. Compounds of the present invention wherein X is O may also be treated with a suitable thionating agent such as P$_2$S$_5$ or Lawesson's Reagent to prepare the instant compounds wherein X is S.

The following schemes represent variations of the general scheme described above.

Scheme 1

Scheme 1 illustrates the preparation of certain endo isomers. The aniline Compound 1b was reductively alkylated with 8-methyl-8-azabicyclo[3:2:1]octan-3-one Compound 1a using sodium borohydride to produce Compound 1c. Arylation of Compound 1c with an appropriately substituted phenyl bromide of the formula 4-bromo-N-R$^2$,R$^3$-benzamide in the presence of a palladium catalyst gave Compound 1d. Upon treatment of Compound 1d with 1-chloroethyl chloroformate, the N-demethylated Compound 1e was obtained. Compound 1e was then converted by alkylation with alkyl halides or reductive alkylation with sodium triacetoxyborohydride and carbonyl compounds to the target Compound 1f.

Scheme 1

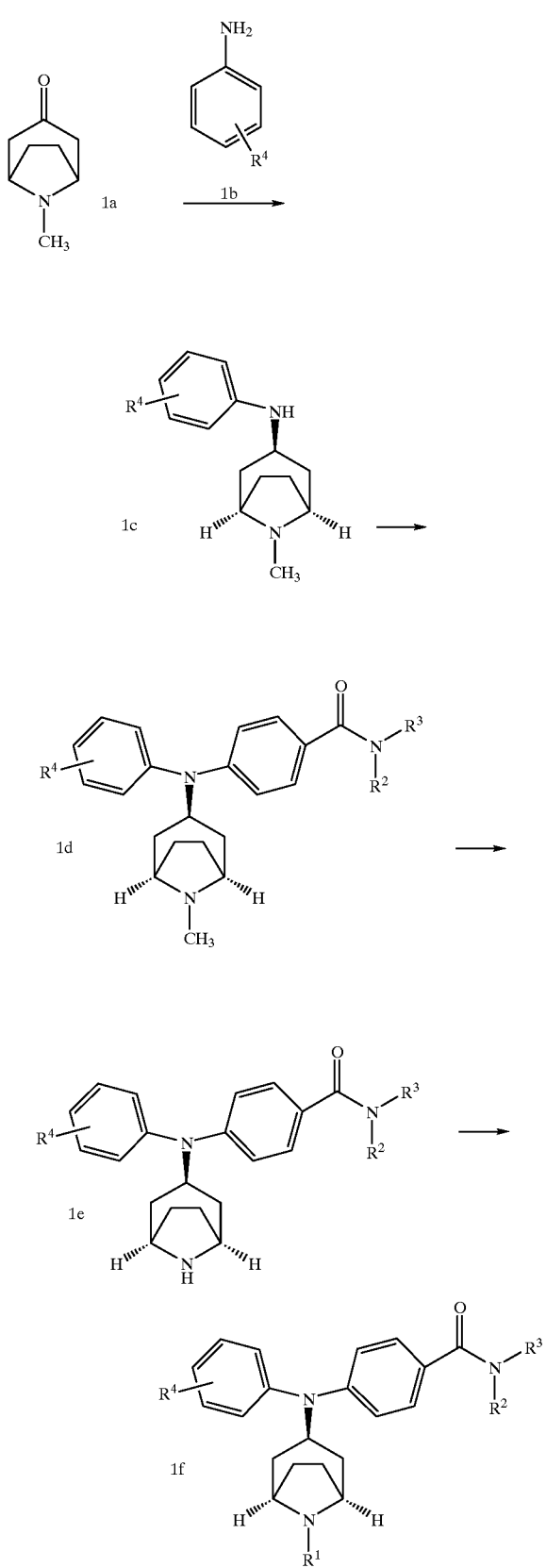

Scheme 2

Scheme 2 is a variation of Scheme 1, wherein the benzylamine Compound 2b was reductively alkylated with 8-methyl-8-azabicyclo[3:2:1]octan-3-one Compound 2a using sodium borohydride to obtain Compound 2c. Arylation of Compound 2c with an appropriately substituted phenyl bromide of the formula 4-bromo-N-$R^2$,$R^3$-benzamide in the presence of a palladium catalyst produced the target Compound 2d.

Scheme 2

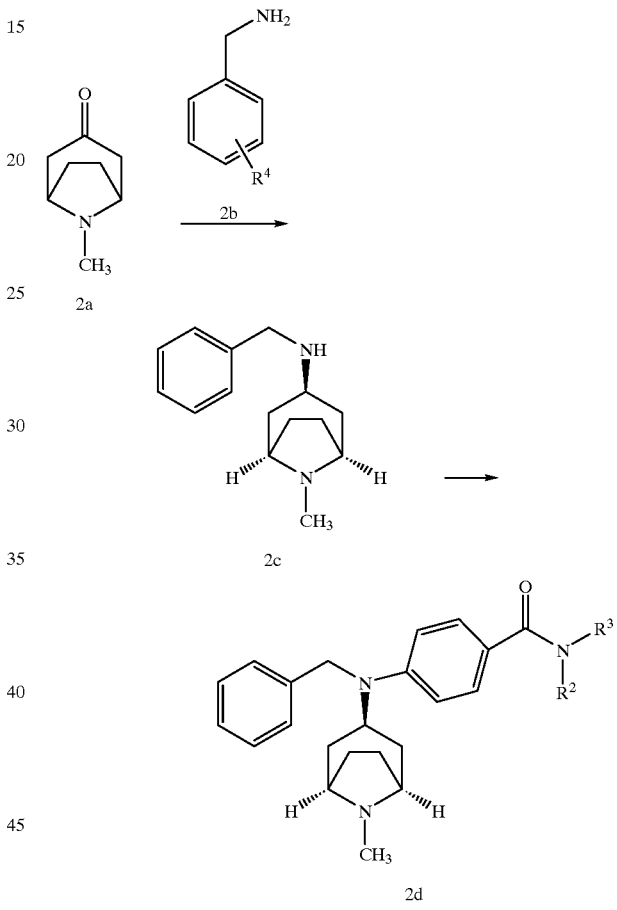

Scheme 3

Scheme 3 illustrates the preparation of certain exo isomers. The aniline Compound 3b was reductively alkylated with 8-methyl-8-azabicyclo[3:2:1]octan-3-one Compound 3a using sodium in ethanol and produced a mixture of Compound 1c and Compound 3c from which Compound 3c was then isolated. Arylation of Compound 3c with an appropriately substituted phenyl bromide of the formula 4-bromo-N-$R^2$,$R^3$-benzamide in the presence of a palladium catalyst gave Compound 3d. Upon treatment of Compound 3d with 1-chloroethyl chloroformate, the N-demethylated Compound 3e was obtained. Compound 3e was then converted by alkylation with alkyl halides or reductive alkylation with sodium triacetoxyborohydride and carbonyl compounds to the target Compound 3f.

Scheme 3

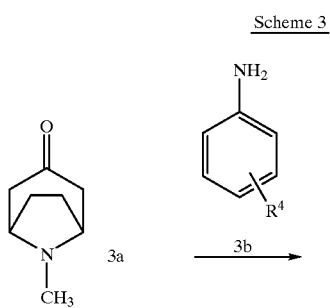

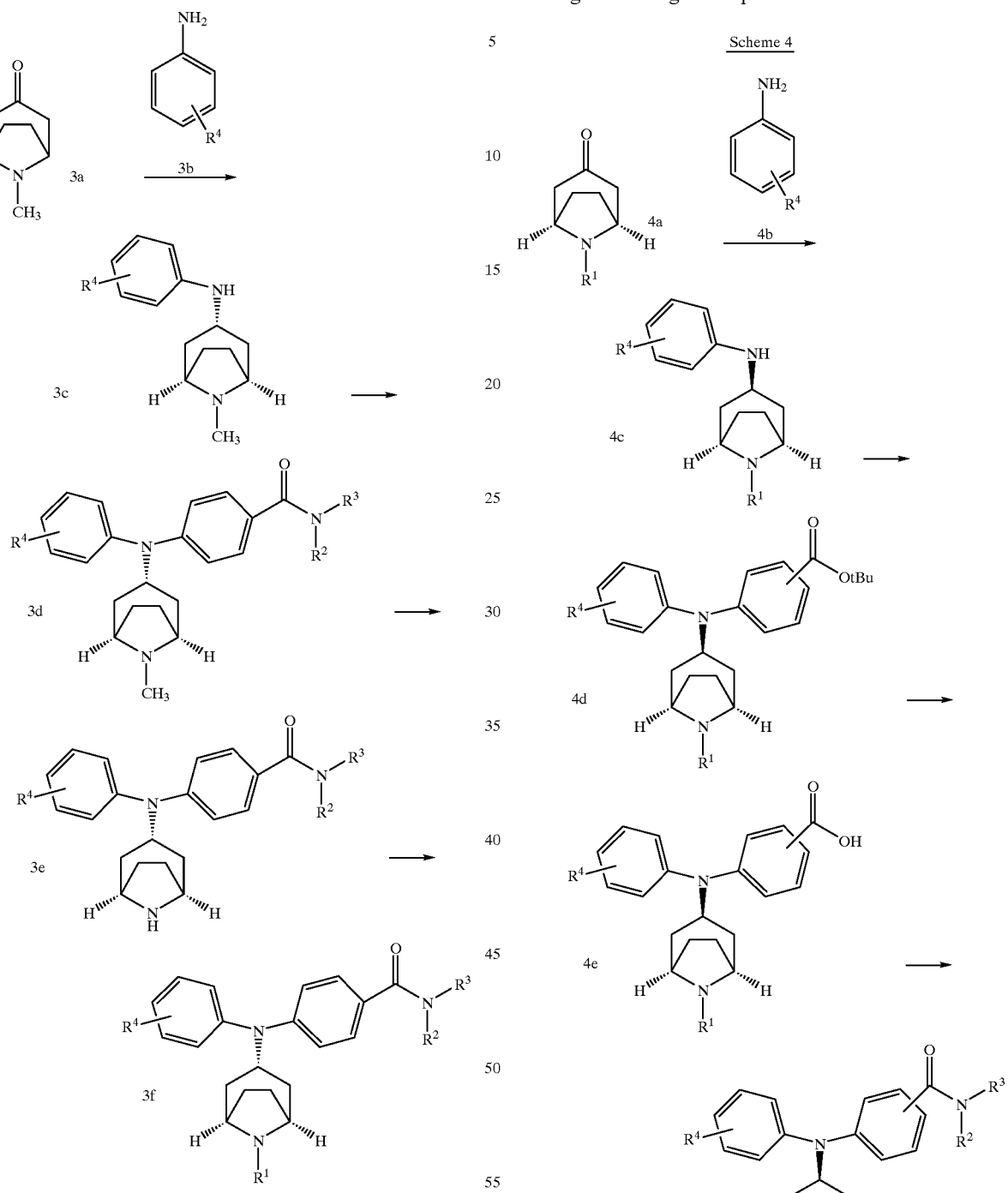

Scheme 4

Scheme 4 illustrates the preparation of certain endo isomers with varying R²—Z—R³ functions via activation of the carboxylic acid. The aniline Compound 4b was reductively alkylated with 8-substituted-8-azabicyclo[3:2:1]octan-3-one Compound 4a in the presence of a hydride reducing agent to produce Compound 4c. Palladium catalyzed arylation of the Compound 4c substrate with t-butyl 3-bromobenzoate or 4-bromobenzoate gave Compound 4d. Cleavage of the t-butyl ester with acid gave rise to the carboxylic acid Compound 4e. Activation of such acids with thionyl chloride or HATU followed by reaction with an amine gave the target Compound 4f.

Scheme 5

Similarly, Scheme 5 illustrates the preparation of certain exo isomers with varying R²—Z—R³ functions via activation of the carboxylic acid. The aniline Compound 5b was reductively alkylated with 8-substituted-8-azabicyclo[3:2:1]

octan-3-one Compound 5a using sodium in ethanol as the reducing agent and produced a mixture from which Compound 5c was separated. Palladium catalyzed arylation of the Compound 5c substrate with t-butyl 4-bromobenzoate gave Compound 5d. Cleavage of the t-butyl ester with acid gave rise to the carboxylic acid Compound 5e. Activation of such acids with thionyl chloride or HATU followed by reaction with an amine produced the target Compound 5f.

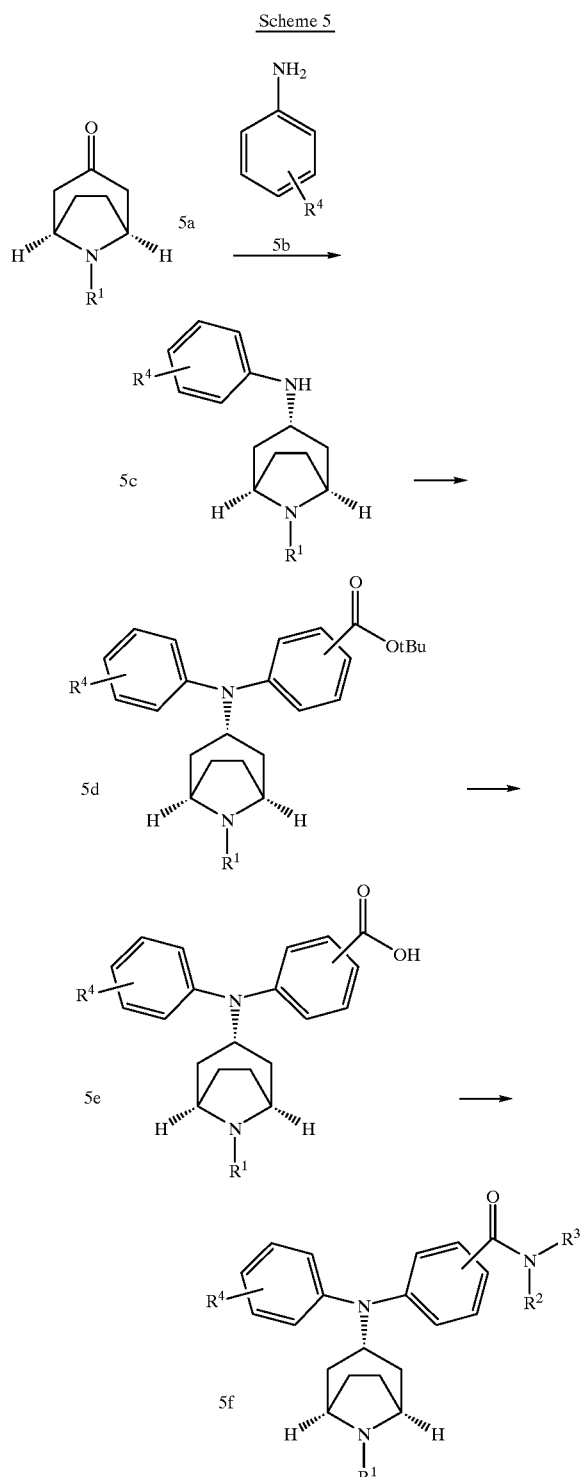

Scheme 5

Specific Synthetic Methods

Specific compounds which are representative of this invention may be prepared as per the following examples offered by way of illustration and not by way of limitation. For the sake of clarity, bracketed numbers following compound names indicate the stoichiometric salt associated with the compound, which is further exemplified by the calculated analytical data. Also, examples specifically used to prepare intermediates for the further synthesis of compounds of the invention are designated by "Procedure." As well, instant compounds may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

EXAMPLE 1

N,N-Diethyl-4-[phenyl(endo-8-methyl-8-azabicyclo [3.2.1]octan-3-yl)amino]benzamide Fumarate [1:1]

A solution of 8-methyl-N-phenyl-endo-8-azabicyclo [3.2.1]octan-3-amine (5.0 g, 23 mmol), N,N-diethyl-4-bromobenzamide (5.9 g, 23 mmol), tris(dibenzylideneacetone)dipalladium(0) (Pd$_2$dba$_3$) (421 mg, 0.46 mmol), tri-tert-butyl phosphine (0.458 mL, 1.84 mmol) and sodium tert-butoxide (2.4 g) in dry toluene (50 mL) was heated at about 110° C. under argon in a pressure vessel for about 16 h. The mixture was cooled and then partitioned between CH$_2$Cl$_2$ and H$_2$O. The organic layer was washed with brine, dried over K$_2$CO$_3$ and then the solvent was evaporated. The resulting brown oil was chromatographed on a Biotage Flash 75 L unit eluted with a 90:10 ratio of CH$_2$Cl$_2$:0.5 M NH$_3$ in MeOH. The title compound was isolated as a yellow oil (7.85 g, 87% yield) and then prepared as a fumarate salt from 2-PrOH and Et$_2$O; mp 184–185° C. MS m/z 392 (MH$^+$). $^1$H NMR 300 MHz (DMSO-d$_6$) δ 7.35–7.45 (t, 2H); 7.12–7.25 (m, 5H); 6.8–6.9 (d, 2H); 6.55 (s, 2H fumaric acid) 4.35–4.45 (m, 1H); 3.3–3.45 (m, 4H); 2.3–2.45 (m, 7H); 1.95–2.05 (m, 2H), 1.6–1.7 (m, 2H); 1.35–1.45 (m, 2H); 1.05–1.15 (t, 6H). Anal. Calcd. for C$_{25}$H$_{33}$N$_3$O.C$_4$H$_4$O$_4$: C, 68.62; H, 7.35; N, 8.28. Found: C, 68.48; H, 7.48; N, 8.16.

Procedure A
N-(3-Methoxyphenyl)-8-methyl-endo-8-azabicyclo[3.2.1]octan-3-amine

A mixture of 8-methyl-8-azabicyclo[3.2.1]octan-3-one (6.95 g, 0.05 mol), m-anisidine (6.2 g, 0.05 mol) and Ti(i-PrO)$_4$ (18.5 mL, 0.625 mol) was heated in an oil bath at about 60° C. overnight. The mixture was removed from the bath and allowed to cool. EtOH (200 mL) was added followed by NaBH$_4$ pellets until the reaction was complete, as judged by absence of the imine. The solvent was evaporated in vacuo and 3N NaOH and EtOAc were added. The mixture was filtered through dicalite and the filtrate transferred to a separation funnel. The aqueous layer was extracted with an additional portion of EtOAc. The organic layers were then combined, washed with brine and dried over K$_2$CO$_3$. The solution was filtered and the solvent was evaporated in vacuo to give a brown oil. Chromatography on silica eluted with a 94:6 ratio of CHCl$_3$:1.0 M NH$_3$ in MeOH gave the title compound (2.6 g, 21% yield).

EXAMPLE 2

N,N-Diethyl-4-[3-methoxyphenyl(endo-8-methyl-8-azabicyclo[3.2.1]octan-3-yl)amino]benzamide Fumarate [1:1]

A mixture of N-(3-methoxyphenyl)-8-methyl-endo-8-azabicyclo[3.2.1]octan-3-amine produced from Procedure A (0.5 g, 2.0 mmol), N,N-diethyl-4-bromocarboxamide (0.62 g, 2.4 mmol), $Pd_2(dba)_3$ (24 mg) and BINAP (47 mg) in toluene (15 mL) was bubbled with argon for about 5 min. NaOt-Bu (0.26 g, 2.75 mmol) was added and the reaction mixture was heated in a sealed tube at about 130° C. for about 48 h. The reaction was then cooled to about rt, diluted with MeCN, filtered and the solvent evaporated in vacuo. The residue was purified by chromatography on silica eluted with a 94:6 ratio of $CHCl_3$:0.5 M $NH_3$ in MeOH. The appropriate fractions were combined and the solvent was evaporated in vacuo. The residue was combined with 1 eq of fumaric acid in 2-PrOH, filtered through dicalite and the solvent evaporated under a stream of nitrogen to give the title compound (0.029 g, 3% yield). MS m/z 422 (MH$^+$). $^1$H NMR (DMSO-d$_6$) δ 1.1 (t, 6H), 1.6 (m, 1H), 2.05 (m, 3H), 2.4 (m, 6H), 3.2 (m, 6H), 3.75 (s, 3H), 4.4 (t, 1H), 6.55 (s, 2H), 6.8 (m, 4H), 7.3 (m, 3H).

EXAMPLE 3

N,N-Diethyl-4-[3-methylthiophenyl(endo-8-methyl-8-azabicyclo[3.2.1]octan-3-yl)amino]benzamide Hydrochloride.

Following Procedure A and Example 2, substituting 3-methylthioaniline for m-anisidine, N,N-diethyl-4-[3-methylthiophenyl(endo-8-methyl-8-azabicyclo[3.2.1]octan-3-yl)amino]benzamide was obtained as the product. MS m/z 438 (MH$^+$). $^1$H NMR (DMSO) δ 10.35 (br s, 1 H); 7.3 (m, 6H); 7.2 (d, 1 H); 7.05 (d, 1 H); 7.0 (dd, 2 H); 4.5 (m, 1 H); 3.75 (s, 2 H); 3.4 (m, 6 H); 2.5 (m, 4 H); 2.3 (m, 64H); 1.9 (d, 2H); 1.1 (m, 6H). Anal. Calc'd. for $C_{26}H_{35}N_3OS \cdot HCl$: C, 65.87; H, 7.65; N, 8.86. Found: C, 66.03; H, 7.52; N, 8.74.

Procedure B
8-Methyl-N-phenylmethyl-endo-8-azabicyclo[3.2.1]octan-3-amine

To a mixture of 8-methyl-8-azabicyclo[3.2.1]octan-3-one (7.0 g, 0.05 mol) and benzylamine (5.4 g, 0.05 mol) in dichloroethane (100 mL), HOAc (2.9 mL) and $Na(OAc)_3BH$ (14.8 g, 0.07 mol) were added and the reaction mixture was stirred overnight at about rt. The reaction was quenched with 3N NaOH and the mixture transferred to a separation funnel. The aqueous layer was extracted with an additional portion of $CHCl_3$. The organic layers were combined and dried over $K_2CO_3$. The solution was then filtered and the solvent evaporated in vacuo to give an oil. The residue was chromatographed on silica eluted with a 95:5 ratio of $CHCl_3$:2.0 M $NH_3$ in MeOH to give the title compound as an oil (4.1 g, 36% yield).

EXAMPLE 4

N,N-Diethyl-4-[phenylmethyl(endo-8-methyl-8-azabicyclo[3.2.1]octan-3-yl)amino]benzamide Trifluoroacetate A mixture of 8-methyl-N-phenylmethyl-endo-8-azabicyclo[3.2.1]octan-3-amine produced from Procedure B (0.92 g, 4.0 mmol), N,N-diethyl 4-bromobenzamide (1.54 g, 6.0 mmol), $Pd_2(dba)_3$ (20 mg) and BINAP (40 mg) in toluene (20 mL) was bubbled with argon for about 5 min. NaOt-Bu (0.58 g, 6.0 mmol) was added and the mixture was heated in a sealed tube at about 130° C. for about 48 h. The reaction was then cooled to about rt, then diluted with MeCN, filtered and the solvent evaporated in vacuo. The residue was purified by chromatography on silica eluted with a 94:6 ratio of $CHCl_3$:0.5 M $NH_3$ in MeOH. The appropriate fractions were combined and the solvent was evaporated in vacuo. This material was further purified by reverse phase HPLC with a gradient of 25–35% MeCN in water with 0.1% TFA. Appropriate fractions were combined and solvent evaporated in vacuo, followed by lyophilization to give the title compound (0.02 g, 1% yield). MS m/z 406 (MH$^+$). $^1$H NMR (DMSO-d$_6$) δ 1.1 (t, 6H), 1.25 (d, 1H), 1.6 (d, 1H), 1.9 (m, 2H), 2.3 (m, 8H), 2.7 (d, 1H), 3.3 (d, 2H), 4.5 (m, 2H), 6.8 (d, 2H), 7.3 (m, 7H).

EXAMPLE 5

N,N-Diethyl-4-[phenyl(enclo-8-azabicyclo[3.2.1]octan-3-yl)amino]benzamide Fumarate [1:1]

A solution of N,N-diethyl-4-[phenyl(endo-8-methyl-8-azabicyclo[3.2.1]octan-3-yl)amino]benzamide (2.40 g, 6.13 mmol) and 1-chloroethyl chloroformate (2.0 mL, 18.5 mmol) in DCE (50 mL) was heated under reflux for about 2 h. Portions of diisopropylethylamine (1.2 mL, 7.0 mmol, and 1-chloroethyl chloroformate (1.0 g, 7.0 mmol) were added and reflux was continued for about 2 h. The solvent was evaporated and a 100 mL portion of MeOH was added. The solution was heated under reflux for about 2 h. The solvent was then evaporated and the residue was partitioned between dilute NaOH solution and $CH_2Cl_2$ The organic layer was dried ($K_2CO_3$) and concentrated. The product N,N-diethyl-4-[phenyl(endo-8-azabicyclo[3.2.1]octan-3-yl)amino]benzamide was obtained as an oil (2.11 g, 91% yield) and further prepared as a fumarate salt from 2-PrOH and TBME; mp 234–235° C. MS m/z 378 (MH$^+$). $^1$H NMR 300 MHz (DMSO-d$_6$) δ 7.37–7.45 (t, 2H), 7.15–7.30 (m, 5H), 6.85–6.9 (d, 2H), 6.4–6.45 (s, 2H fumaric acid), 4.4–4.5 (m, 1H), 3.25–3.35 (m, 2H), 3.2–3.4 (m, 4H), 2.25–2.4 (m, 2H), 1.7–1.9 (m, 4H), 1.4–1.5 (m, 2H), 1.05–1.15 (t, 6H). Anal. Calcd. for $C_{24}H_{31}N_3O \cdot C_4H_4O_4 \cdot 0.5\ H_2O$: C, 66.91; H, 7.22; N, 8.36. Found: C, 66.64; H, 7.24; N, 8.04.

EXAMPLE 6

N,N-Diethyl-4-[phenyl(endo-8-phenethyl-8-azabicyclo[3.2.1]octan-3-yl)amino]benzamide Fumarate [1:1]

A mixture of N,N-diethyl-4-[phenyl(endo-8-azabicyclo [3.2.1]octan-3-yl)amino]benzamide (1.0 g, 2.65 mmol), phenylacetaldehyde (0.51 mL, 4.3 mmol) and sodium triacetoxyborohydride (2.0 g, 9.4 mmol) in DCE (75 mL) was stirred for about 16 h. The reaction mixture was partitioned between dilute sodium hydroxide and $CH_2Cl_2$. The organic layer was dried ($K_2CO_3$) and concentrated. The product N,N-diethyl-4-[phenyl(endo-8-phenethyl-8-azabicyclo [3.2.1]octan-3-yl)amino]benzamide (1.25 g, 98% yield) was obtained. A fumarate salt was prepared in 2-PrOH; mp 122–123° C. MS m/z 482 (MH$^+$). $^1$H NMR 300 MHz (DMSO-d$_6$) δ 7.40–7.45 (t, 2H), 7.15–7.35 (m, 8H), 7.05–7.12 (d, 2H), 6.65–6.70 (d, 2H), 6.58 (s, 2H fumaric acid), 4.30–4.40 (m, 1H), 3.40–3.50 (m, 2H), 3.25–3.35 (m, 4H), 2.75–2.80 (t, 2H), 2.55–2.60 (t, 2H), 2.30–2.40 (m, 2H), 1.90–2.0 (m, 2H), 1.40–1.50 (m, 2H), 1.05–1.15 (t, 6H). Anal. Calcd. for $C_{32}H_{39}N_3O \cdot C_4H_4O_4 \cdot 0.5\ H_2O$: C, 71.26; H, 7.31; N, 6.93. Found: C, 71.46; H, 7.90; N, 6.36.

EXAMPLES 7–9

Following the procedure of Example 6 and substituting the appropriate carbonyl compound for phenylacetaldehyde the following compounds were prepared:

| Ex# | Carbonyl Compound | R¹ | MS m/z (MH⁺) |
|---|---|---|---|
| 7 | Propionaldehyde | n-propyl | 420 |
| 8 | cyclohexanone | cyclohexyl | 460 |
| 9 | piperonal | piperonyl | 512 |

EXAMPLE 10

N,N-Diethyl-4-[phenyl(endo-8-allyl-8-azabicyclo[3.2.1]octan-3-yl)amino]benzamide Trifluoroacetate A mixture of N,N-diethyl-4-[phenyl(endo-8-azabicyclo[3.2.1]octan- 3-yl)amino]benzamide (0.170 g, 0.45 mmol), allyl bromide (0.04 mL, 0.45 mmol) and potassium carbonate (0.25 g, 1.8 mmol) in $CH_3CN$ (10 mL) was stirred for about 16 h. The solid was filtered and the solvent evaporated from the filtrate. The product was purified by reverse phase HPLC on a Gilson automated system to yield (0.04 g, 21% yield) N,N-diethyl-4-[phenyl(endo-8-allyl-8-azabicyclo[3.2.1]octan-3-yl)amino]benzamide as the trifluoroacetate salt. MS m/z 418 (MH⁺). ¹H NMR 300 MHz (acetonitrile-$d_3$) δ 7.25–7.60 (m, 9H), 5.95–6.10 (m, 1H), 5.50–5.60 (d, 2H), 4.50–4.60 (m, 1H), 3.80–3.90 (m, 2H), 3.55–3.65 (t, 2H), 3.30–3.55 (m, 3H), 2.5–2.65 (m, 4H), 2.00–2.40 (m, 5H), 1.15–1.40 (t, 6H).

EXAMPLE 11

N,N-Diethyl-4-[phenyl(exo-8-methyl-8-azabicyclo[3.2.1]octan-3-yl)amino]benzamide Fumarate A solution of exo-N-phenyl-8-methyl-8-azabicyclo[3.2.1] (1.3 g, 6 mmol), N,N-diethyl-4-bromobenzamide (1.84 g, 7.2 mmol), sodium t-butoxide (0.75 g, 7.8 mmol), tri-t-butylphosphine (0.1 mL, 0.48 mmol) and tris(dibenzylideneacetone)-dipalladium(0) ($Pd_2dba_3$) (110 mg, 0.0.12 mmol) in dry toluene (10 mL) was heated to about 100° C. under argon in a pressure vessel for about 16 h. The mixture was then cooled and partitioned between $CH_2Cl_2$ and $H_2O$. The organic layer was washed with brine, then dried ($K_2CO_3$) and the solvent evaporated. The residue was chromatographed on a Biotage Flash 40 eluted with a 90:10 ratio of $CH_2Cl_2$:0.5 M $NH_3$ in MeOH hexane. There was obtained N,N-diethyl-4-[phenyl(exo-8-methyl-8-azabicyclo[3.2.1]octan-3-yl)amino]benzamide (2.3 g, 98% yield) as an oil. A fumarate salt was prepared from 2-PrOH and collected as a white solid; mp 128–130° C. MS m/z 347 (MH⁺). ¹H NMR 300 MHz (DMSO-$d_6$) δ 7.4 (t, 2H); 7.25 (t, 1H); 7.2 (d, 2H); 7.0 (d, 2H); 6.6 (d, 2H); 6.4 (s, 1H); 4.3 (m, 1H); 3.5 (m,2H); 3.3 (q, 4H); 2.3 (s, 3H); 1.8–2.2 (m, 6H); 1.7 (t, 2H); 1.1 (t, 6H). Anal. Calcd. for $C_{29}H_{37}N_3O_2.0.5\ C_2H_2O_4$: C, 68.62; H, 7.35; N,8.28. Found: C, 68.21; H, 7.23; N, 8.17.

EXAMPLE 12

N,N-Di-n-propyl-4-[phenyl(exo-8-methyl-8-azabicyclo[3.2.1]octan-3-yl)amino]benzamide Following the procedure of Example 11 and substituting N,N-di-n-propyl-4-bromobenzamide for N,N-diethyl-4-bromobenzamide, the product N,N-di-n-propyl-4-[phenyl(exo-8-methyl-8-azabicyclo[3.2.1]octan-3-yl)amino]benzamide was obtained. MS m/z 420 (MH⁺). ¹H NMR 300 MHz (CDCl₃) δ 7.35 (t, 2H); 7.2 (m, 8H); 7.0(d, 2H); 6.6 (d, 2H); 6.4 (s, 1H); 4.3(m, 1H); 3.3 (m, 4H): 3.2 (m, 2H); 2.2 (s, 3H); 2.15 (m, 2H); 1.8–1.5 (m, 14H); 0.9 (m, 6H).

EXAMPLE 13

N,N-Diethyl-4-[phenyl(exo-8-azabicyclo[3.2.1]octan-3-yl)amino]benzamide

A solution of N,N-diethyl-4-[phenyl(exo-8-methyl-8-azabicyclo[3.2.1]octan-3-yl)amino]benzamide (1.67 g, 4.27 mmol) and 1-chloroethyl chloroformate (1.37 mL, 12.8 mmol) in DCE (35 mL) was heated under reflux for about 2 h. Portions of triethylamine (0.85 mL, 6.1 mmol) and 1-chloroethyl chloroformate (0.7 g, 1.8 mmol) were added and reflux was continued for about another 2 h. The solvent was evaporated and a 100 mL portion of MeOH was added. The solution was heated under reflux for about 2 h. The solvent was then evaporated and the residue was partitioned between dilute NaOH solution and $CH_2Cl_2$. The organic layer was dried ($K_2CO_3$) and concentrated. There was obtained N,N-diethyl-4-[phenyl(exo-8-azabicyclo[3.2.1]octan-3-yl)amino]benzamide (1.5 g, 93% yield) as an oil. MS m/z 378 (MH⁺). ¹H NMR 300 MHz (CDCl₃) δ 7.4 (t, 2H); 7.2 (m, 3H); 7.0(d, 2H); 6.6 (d, 2H); 4.3(m, 1H); 3.7 (m,2H); 3.4 (m, 4H); 2.0–1.8 (m, 6H); 1.6 (t, 2H).

EXAMPLE 14

N,N-Di-n-propyl-4-[phenyl(exo-8-azabicyclo[3.2.1]octan-3-yl)amino]benzamide

Following the procedure of Example 13 and substituting N,N-di-n-propyl-4-[phenyl(exo-8-methyl-8-azabicyclo[3.2.1]octan-3-yl)amino]benzamide for N,N-diethyl-4-[phenyl(exo-8-methyl-8-aza bicyclo[3.2.1]octan-3-yl)amino]benzamide, the product N,N-di-n-propyl-4-[phenyl(exo- 8-azabicyclo[3.2.1]octan-3-yl)amino]benzamide was obtained. MS m/z 406 (MH⁺).

EXAMPLE 15

N,N-Diethyl-4-[phenyl(exo-8-hexyl-8-azabicyclo[3.2.1]octan-3-yl)amino]benzamide Fumarate [1:1]

A mixture of N,N-diethyl-4-[phenyl(exo-8-azabicyclo[3.2.1]octan-3-yl)amino]benzamide (1.0 g, 2.65 mmol), sodium triacetoxyborohydride (0.84 g, 4.0 mmol) and n-hexanal (0.38 mL, 3.18 mmol) in DCE (10 mL) was stirred for about 16 h. Second portions of sodium triacetoxyborohydride (0.84 g, 4.0 mmol) and n-hexanal (0.38 mL, 3.18 mmol) were added and the mixture stirred for about 3 h. The reaction mixture was then partitioned between dilute sodium hydroxide and $CH_2Cl_2$. The organic layer was dried ($K_2CO_3$) and concentrated. The residue was flash chromatographed eluted with a 90:10 ratio of $CH_2Cl_2$:0.5 M $NH_3$ in MeOH. There was obtained N,N-diethyl-4-[phenyl(exo-8-hexyl-8-azabicyclo[3.2.1]octan-3-yl)amino]benzamide (0.27 g, 22% yield). A fumarate salt was prepared in 2-PrOH; mp 182–183° C. MS m/z 462 (MH⁺). ¹H NMR 300 MHz (DMSO-$d_6$) δ 7.4 (t, 2H); 7.3 (t, 1H); 7.2(d, 2H); 7.0(d, 2H); 6.6 (d, 2H); 6.5 (s, 1H); 4.3(m, 1H); 3.3 (m,8H); 2.4 (m, 2H); 2.1–1.8 (m, 6H); 1.66 (t, 2H); 1.4 (m, 2H); 1.1(t, 6H); 0.8 (t, 3H). Anal. Calcd. for $C_{30}H_{43}N_3O.C_4H_4O_4$: C, 70.68; H, 8.20; N,7.27. Found: C, 70.12; H, 8.29; N, 7.15.

EXAMPLES 16–26

Following the procedure of Example 15 and substituting the appropriate carbonyl compound for n-hexanal the following compounds were prepared:

| Ex# | Carbonyl Compound | R⁴ | MS m/z (MH⁺) |
|---|---|---|---|
| 16 | propionaldehyde | n-propyl | 420 |
| 17 | phenylacetaldehyde | phenethyl | 482 |
| 18 | diphenylacetaldehyde | 2,2-diphenylethyl | 558 |
| 19 | cyclohexanecarboxaldehyde | cyclohexylmethyl | 474 |
| 20 | 2-ethylbutyraldehyde | 2-ethylbutyl | 462 |
| 21 | 2-furancarboxaldehyde | 2-furylmethyl | 458 |
| 22 | piperonal | 3,4-methylenedioxybenzyl | 512 |
| 23 | 3,3-dimethylacrolein | 3,3-dimethallyl | 446 |
| 24 | 3,4-dimethoxyphenylacetaldehyde | 3,4-dimethoxyphenethyl | 542 |
| 25 | 4-fluorophenylacetaldehyde | 4-fluorophenethyl | 500 |
| 26 | phenylpropionaldehyde | phenylpropyl | 496 |

EXAMPLE 27

N,N-Di-n-propyl-4-[phenyl(exo-8-phenethyl-8-azabicyclo[3.2.1]octan-3-yl)amino]benzamide Following the procedure of Example 15 and substituting N,N-di-n-propyl-4-[phenyl(exo-8-azabicyclo[3.2.1]octan-3-y)amino]benzamide for N,N-diethyl-4-[phenyl(exo-8-azabicyclo[3.2.1]octan-3-yl)amino]benzamide and phenylacetaldehyde for hexanal, the product N,N-di-n-propyl-4-[phenyl(exo-8-phenethyl-8-azabicyclo[3.2.1]octan-3-yl)amino]benzamide was obtained. MS m/z 510 (MH⁺). $^1$H NMR 300 MHz (CDCl$_3$) δ 7.4 (t, 2H); 7.3–7.2 (m, 8H); 7.1 (d, 2H); 7.0 (dd, 2H); 6.6 (dd, 2H); 4.3 (m, 1H); 3.4 (m, 6H); 2.65 (m, 2H); 2.5 (m, 2H); 2.0 (m, 2H); 1.8–1.6 (m, 6H); 0.9 (m, 6H).

EXAMPLE 28

1,1-Dimethylethyl 4-[phenyl(endo-8-methyl-8-azabicyclo[3.2.1]octan-3-yl)amino]benzoate A solution of endo-N-phenyl-8-methyl-8-azabicyclo[3.2.1]octanamine (5.0 g, 23 mmol), t-butyl 4-bromobenzoate (6.0 g, 23 mmol), tris(dibenzylideneacetone) dipalladium(0) (Pd$_2$dba$_3$) (425 mg, 0.46 mmol), tri-tert-butyl phosphine (0.46 mL, 1.84 mmol) and sodium tert-butoxide (2.7 g) in dry toluene (30 mL) was heated at about 110° C. under argon in a pressure vessel for about 16 h. The mixture was cooled then partitioned between CH$_2$Cl$_2$ and 3N NaOH. The organic layer was then washed with brine, dried over K$_2$CO$_3$ and the solvent evaporated. The resulting brown oil was chromatographed on a Biotage Flash 75 L unit eluted with a 90:10 ratio of CH$_2$Cl$_2$:0.5 M NH$_3$ in MeOH. The title compound was recrystallized from EtOAc/hexane to afford the title compound (7.5 g, 83% yield) as a white powder; mp 150–152° C. MS m/z 393 (MH⁺). $^1$H NMR 300 MHz (CDCl$_3$) δ 7.7–7.8 (d, 2H); 7.35–7.45 (t, 2H); 7.25–7.35 (t, 1H); 7.0–7.1 (d, 2H); 6.55–6.60 (d, 2H); 4.45–4.55 (m, 1H); 3.45 (s, 3H); 3.15–3.25 (m, 2); 2.45–2.6 (m, 3H).

EXAMPLE 29

4-[phenyl(endo-8-methyl-8-azabicyclo[3.2.1]octan-3-yl)amino]benzoic acid Trifluoroacetate A solution of 1,1-dimethylethyl 4-[phenyl(endo-8-methyl-8-azabicyclo[3.2.1]octan-3-yl)amino]benzoate produced in Example 28 (3.65 g, 9.28 mmol) and TFA (5 mL) in CH$_2$Cl$_2$ (50 mL) was stirred for about 1 h. The solvent was evaporated to yield 4-[phenyl(exo-8-methyl-8-azabicyclo[3.2.1]octan-3-yl)amino]benzoic acid (3.10 g, 99.5% yield) as the trifluoroacetate salt. MS m/z 337 (MH⁺). $^1$H NMR 300 MHz (DMSO-d$_6$) δ 7.65–7.75 (d, 2H), 7.2–7.3 (t, 2H), 6.85–6.9 (t, 1H), 6.75–6.8 (d, 2H), 6.7–6.75 (d, 2H), 4.25–4.35 (m, 1H), 3.3–3.4 (m, 4H), 3.05–3.1 (m, 2H), 2.2–2.4 (m, 2H), 2.05 (s, 3H), 1.9–2.0 (m, 2H).

EXAMPLE 30

N,N-Dimethyl-4-[phenyl(endo-8-methyl-8-azabicyclo[3.2.1]octan-3-yl)amino]benzamide Trifluoroacetate A solution of 4-[phenyl(endo-8-methyl-8-azabicyclo[3.2.1]octan-3-yl)amino]benzoic acid (0.050 g, 0.14 mmol), HATU (0.053 g, 0.14 mmol), diisopropylethylamine (0.1 mL, 0.56 mmol) and dimethylamine (0.25 mL, 0.5 mmol; 40% by weight in water) in DMF (2 mL) was stirred for about 1 h. The reaction mixture was diluted with water (1 mL) and the product was isolated by reverse phase HPLC on a Gilson automated system to afford N,N-Dimethyl-4-[phenyl(endo-8-methyl-8-azabicyclo[3.2.1]octan-3-yl)amino]benzamide trifluoroacetate (50 mg, 100% yield). MS m/z 364 (MH⁺). $^1$H NMR 300 MHz δ 7.18–7.4 (m, 9H), 4.35–4.4 (m, 1H), 3.65–3.75 (m, 2H), 2.95 (s, 6H), 2.65 (s, 3H), 2.3–2.4 (m, 4H), 2.15–2.25 (m, 2H), 2.0–2.1 (m, 2H).

EXAMPLE 31

1-[4-phenyl(endo-8-methyl-8-azabicyclo[3.2.1]octan-3-yl)amino]benzoylpyrrolidine Trifluoroacetate To a flask containing toluene (10 mL) under N$_2$ cooled on an ice bath, 2M trimethylaluminum (0.4 mL) in toluene (0.80mmol) and pyrrolidine (0.067 mL, 0.80 mmol) were added. The solution was brought to rt, then toluene (5 mL) containing 1,1dimethylethyl-4-[phenyl(endo-8-methyl-8-azabicyclo[3.2.1]octan-3-yl)amino]benzoate (100 mg, 0.26 mmol) was added and heated to reflux for about 16 h. The reaction mixture was cooled and partitioned between dilute NaOH and CH$_2$Cl$_2$. The organic fractions were then combined, washed with brine, dried over K$_2$CO$_3$, filtered and concentrated. The product was purified by reverse phase HPLC on a Gilson automated system to afford 1-[4-phenyl(endo-8-methyl-8-azabicyclo[3.2.1 ]octan-3-yl)amino]benzoylpyrrolidine trifluoroacetate (35 mg, 35% yield). MS m/z 390 (MH⁺). $^1$H NMR 300 MHz (CDCl$_3$) δ 7.1–7.6 (m, 9H), 4.4–4.55 (m, 1H), 3.35–3.7 (m, 6H), 2.6–2.8 (m, 5H), 2.4–2.6 (d, 2H), 1.75–2.30 (m, 8H).

EXAMPLES 32–37

Following the procedure of Example 30 and substituting the appropriate amine for dimethylamine, the following compounds were prepared:

| Ex# | Amine | R² | R³ | MS m/z (MH⁺) |
|---|---|---|---|---|
| 32 | ethyl,methylamine | ethyl | methyl | 378 |
| 33 | ethyl,(2-methyl)allylamine | ethyl | 2-methylallyl | 418 |
| 34 | ethyl,(4-methyl)benzylamine | ethyl | 4-methylbenzyl | 468 |
| 35 | propyl, butylamine | propyl | butyl | 434 |

-continued

| Ex# | Amine | R² | R³ | MS m/z (MH⁺) |
|---|---|---|---|---|
| 36 | N-methylaniline | methyl | phenyl | 426 |
| 37 | dipropylamine | propyl | propyl | 420 |

EXAMPLE 38

1,1-Dimethylethyl 3-[phenyl(endo-8-methyl-8-azabicyclo[3.2.1]octan-3-yl)amino]benzoate A solution of N-phenyl-8-methyl-8-azabicyclo[3.2.1]octanamine (5.6 g, 25.8 mmol), t-butyl 3-bromobenzoate (6.64 g, 25.8 mmol), sodium t-butoxide (3.1 g, 32.3 mmol), tris(dibenzylideneacetone)-dipalladium(0) ($Pd_2dba_3$) (0.47 g, 0.5 mmol) and tri-t-butylphosphine (0.50 mL, 2.0 mmol) in dry toluene (40 mL) was heated at about 100° C. under argon in a pressure vessel for about 20 h. The mixture was cooled and partitioned between $CH_2Cl_2$ (200 mL) and $H_2O$ (200 mL). The organic layer was then washed with water and brine, dried ($Na_2SO_4$) and the solvent evaporated. The residue was purified by flash chromatography on silica gel eluted with a 10–30:1 ratio of $CH_3OH:NH_4OH$ in $CH_2Cl_2$ to give the product as an amber oil (0.7 g, 7% yield). MS m/z 393 (MH⁺). ¹H NMR 300 MHz ($CDCl_3$) δ 1.32–1.43 (m, 2 H), 1.49–1.60 (m, 2 H) superimposed on 1.57 (s, 9 H), 1.98–2.07 (m, 2 H), 2.19 (s, 3 H), 2.35–2.47 (m, 2 H), 3.12–3.20 (m, 2 H), 4.32–4.44 (m, 1 H), 6.95–7.10 (m, 3 H), 7.21–7.33 (m, 4 H) and 7.51–7.56 (m, 2 H).

EXAMPLE 39

3-[Phenyl(endo-8-methyl-8-azabicyclo[3.2.1]octan-3-yl)amino]benzoic Acid Dihydrochloride A mixture of 1,1-Dimethylethyl 3-[phenyl(endo-8-methyl-8-azabicyclo[3.2.1]octan-3-yl)amino]benzoate (0.7 g, 1.8 mmol) in 4N HCl (10.5 mL) was heated to about 65° C. for about 1.5 h. The reaction mixture was cooled to about rt and the resultant solid was collected by filtration. The product was washed with water and triturated with $Et_2O$ to give the product as a beige solid (0.7 g). MS m/z 337 (MH⁺). ¹H NMR(DMSO-$d_6$) δ 1.74–1.93 (m, 2H), 2.10–2.37 (m, 4 H), 2.50–2.60 (s, 3 H superimposed on a m, 2 H), 3.71 (br s, 2 H), 4.53 (br s, 1 H), 7.17 (t, 1 H), 7.20–7.50 (m, 7 H), 7.58–7.69 (m, 2 H), 7.77 (s,1 H) and 10.9 (br s, 1 H).

EXAMPLE 40

N,N-Diethyl-3-[phenyl(endo-8-methyl-8-azabicyclo[3.2.1]octan-3-yl)amino]benzamide Bistrifluoroacetate A solution of 3-[Phenyl(endo-8-methyl-8-azabicyclo[3.2.1]octan-3-yl)amino]benzoic acid dihydrochloride (50 mg, 0.122 mmol), HBTU (51 mg, 0.134 mmol) and N,N-diisopropylethylamine (0.087 mL, 0.50 mmol) in DMF (1 mL) was stirred at about rt for about 5 min. Diethylamine (0.038 mL, 0.366 mmol) was added to the solution and stirring was continued for about an additional 2 h. Water (0.300 mL) was added and the solution was stirred for about 10 min. The solution was applied to a $C_{18}$ reverse phase column and eluted with a 10:90:0.1 to 90:10:0.1 gradient ratio of $CH_3CN:H_2O:TFA$ to give the product as the bistrifluoroacetate (15 mg, 20% yield). MS m/z 392 (MH⁺). ¹H NMR ($CD_3OD$) δ 1.03 (t, 3 H), 1.24 (t, 3 H), 2.12–2.33 (m, 6 H), 2.54–2.63 (m, 2 H), 2.74 (s, 3 H), 3.18 (q, 2 H), 3.53 (q, 2 H), 3.73–3.80 (br m, 2 H), 4.42 (br m, 1 H), 7.05 (m, 1 H), 7.18 (t, 1 H), 7.30–7.46 (mi, 7 H).

EXAMPLE 41

1,1-Dimethylethyl 4-[phenyl(endo-8-(2-phenylethyl)-8-azabicyclo[3.2.1]octan-3-yl)amino]benzoate A solution of endo-N-phenyl-8-(2-phenylethyl)-8-azabicyclo[3.2.1]octanamine (3.47 g, 11.3 mmol), t-butyl 4-bromobenzoate (3.49 g, 13.57 mmol), sodium t-butoxide (1.5 g, 15.87 mmol), tris(dibenzylideneacetone)-dipalladium(0) ($Pd_2dba_3$) (200 mg, 0.022 mmol) and tri-t-butylphosphine (0.17 mL, 0.68 mmol) in dry toluene (20 mL) was heated at about 100° C. under argon in a pressure vessel for about 16 h. The mixture was cooled and then partitioned between $CH_2Cl_2$ and $H_2O$. The organic layer was washed with brine, dried ($K_2CO_3$) and the solvent evaporated. The residue was flash chromatographed and eluted with 20% acetone in hexane. There was obtained 1,1-dimethylethyl 4-[phenyl(endo-8-(2-phenylethyl)-8-azabicyclo[3.2.1]octan-3-yl)amino]benzoate (4.5 g, 83% yield) as a golden oil. MS m/z 483 (MH⁺). ¹H NMR ($CDCl_3$) δ 7.7 (d, 2 H); 7.4 (t, 2 H); 7.3–7.2 (m, 3 H); 7.0 (dd, 2H); 6.5 (d, 2 H); 4.5 (m, 1 H); 3.3 (br s, 2 H); 2.8 (t, 2 H); 2.4 (m, 4 H); 1.9 (m, 2 H); 1.6 (m, 4 H); 1.5 (s, 9 H).

EXAMPLE 42

4-[Phenyl(endo-8-(2-phenylethyl)-8-azabicyclo[3.2.1]octan-3-yl)amino]benzoic Acid Hydrochloride A sample of 1,1-dimethylethyl 4-[phenyl(endo-8-(2-phenylethyl)-8-azabicyclo[3.2.1]octan-3-yl)amino]benzoate (4.0 g, 8.3 mmol) was heated at about 95° for about 3 h in 6N HCl. The mixture was then cooled and the solid 4-[phenyl(endo-8-(2-phenylethyl)-8-azabicyclo[3.2.1]octan-3-yl)amino]benzoic acid hydrochloride was collected as a white solid. MS m/z 427 (MH⁺). ¹H NMR (DMSO) δ 10.35 (s, 1 H); 7.7 (t, 2 H); 7.5 (t, 2 H); 7.3–7.1 (m, 3 H); 7.0 (dd, 2 H); 4.7 (m, 1 H); 3.9 (m, 2 H); 2.6 (m, 2 H); 2.2 (m, 2 H); 2.0–1.8 (m, 6 H).

EXAMPLE 43

N,N-Dimethyl-4-[phenyl(endo-8-(2-phenylethyl)-8-azabicyclo[3.2.1]octan-3-yl)amino]benzamide Fumarate A solution of 4-[phenyl(endo-8-(2-phenylethyl)-8-azabicyclo[3.2.1]octan-3-yl)amino]benzoic acid hydrochloride from Example 23 (1.0 g, 2.0 mmol) and thionyl chloride (0.44 mL) in $CHCl_3$ (4 mL) was heated under reflux for about 2 h. The solvent was evaporated and the residue taken up in $CH_2Cl_2$ (8 mL) and added to a stirred solution of 1 N NaOH (4 mL) and 40% aqueous dimethylamine solution (4 mL). The mixture was stirred for about 30 min and the organic layer then separated and concentrated. The residue was flash chromatographed eluted with 50% acetone in hexane. The product N,N-dimethyl-4-[3-phenyl[endo-8-(2-phenylethyl)-8-azabicyclo[3.2.1]octan-3-yl]amino]benzamide (0.45 g, 50% yield) was obtained as an oil. A fumarate salt was prepared in 2-PrOH/$Et_2O$; mp 114–115° C. MS m/z 454 (MH⁺). ¹H NMR ($CDCl_3$) δ 7.4–7.2 (m, 10 H); 7.0 (dd, 2 H); 6.65 (dd, 2 H); 4.5 (m, 1 H); 3.3 (m, 2 H); 3.0 5 (s, 6 H); 2.8 (t, 2 H); 2.4 (m, 4 H); 1. 9 (m, 2 H); 1.3 (d, 2 H), 1.2 (t, 2 H).

EXAMPLES 44–50

Following the procedure of the Example 43 and substituting the appropriate $R^3$ and $R^2$ amine for dimethylamine, the following N,N-$R^3$,$R^2$-4-[3-phenyl[endo-8-(2-phenylethyl)-8-azabicyclo[3.2.1]octan-3-yl]amino] benzamides were obtained as products:

| Ex# | $R^2$ | $R^3$ | MS m/z (MH+) |
|---|---|---|---|
| 44 | $CH_3$ | $C_2H_5$ | 468 |
| 45 | $C_2H_5$ | n-butyl | 510 |
| 46 | n-propyl | n-propyl | 510 |
| 47 | $CH_3$ | n-propyl | 482 |
| 48 | $CH_3$ | n-butyl | 496 |
| 49 | $C_2H_5$ | 2-methallyl | 508 |
| 50 | | pyrrolidinyl | 480 |

EXAMPLE 51

N,N-Diethyl-4-[phenyl(endo-8-methyl-8-azabicyclo [3.2.1]octan-3-yl)amino]benzenecarbothioamide Trifluoroacetate A solution of endo-N-phenyl-8-methyl-8-azabicyclo [3.2.1]octanamine (0.25 g, 0.64 mmol) and (0.37 g, 0.9 mmol) Lawesson's reagent in benzene (20 mL) was stirred at about 60° C. for about 3 h. The reaction was then cooled and partitioned between $CH_2Cl_2$ and water. The organic fractions were combined, washed with yellow brine and dried over $K_2CO_3$. The solvent was evaporated and the yellow oil was purified by Gilson automated HPLC to yield 0.015 g of the trifluoroacetate salt. MS m/z 408.40 (MH+). $^1$H NMR 300 MHz (acetonitrile-$d_3$) δ 7.4–7.6 (m, 4H); 7.18–7.4 (m, 5H); 4.5–4.6 (m, 1H); 4.15–4.25 (m, 2H); 3.7–3.85 (m, 2H); 3.5–3.6 (m, 2H); 2.7 (s, 3H); 2.55–2.65 (d, 2H); 2.4–2.55 (d, 2H); 2.2–2.35 (m, 2H); 2.05–2.18 (d, 2H); 1.4–1.5 (t, 3H); 1.15–1.25 (t, 3H).

Procedure C 3-(3-methoxyphenyl)amino-endo-8-azabiyclo[3.2.1]octane-8-carboxylic acid 1,1-dimethylethyl ester following Procedure B and substituting 3-oxo-8-azabicyclo[3.2.1]octane-8-carboxylic acid 1,1-dimethylethyl ester and m-anisidine for 8-methyl-8-azabicyclo[3.2.1]octanone and benzylamine with omission of HOAc, the product 3-(3-methoxyphenyl)amino-endo-8-azabicyclo[3.2.1]octane-8-carbolic acid 1,1-dimethylethyl ester was produced. The product was purified by silica gel chromatography eluted with 10% acetone in hexane. MS m/z 333 (MH+).

Procedure D

3-[[3-[[(3-Fluorophenyl)methylamino]carbonyl]phenyl] (3-methoxyphenyl)amino]-endo-8-azabicyclo[3.2.1]octane-8-carboxylic acid 1,1-dimethyleithyl ester Following the procedure of Example 1 and substituting the 3-(3-methoxyphenyl)amino-endo-8-azabicyclo[3.2.1] octane-8-carboxylic acid 1,1-dimethylethyl ester obtained in Procedure C and N-(3-fluorophenyl)-N-methyl-3-bromobenzamide for 8-methyl-N-phenyl-endo-8-azabicyclo [3.2.1]octan-3-amine and N,N-diethyl-4-bromobenzamide obtained the product 3-[[3-[[(3-fluorophenyl)methylamino] carbonyl]phenyl](3-methoxyphenyl)amino]-endo-8-azabicyclo[3.2.1]octane-8-carboxylic acid 1,1-dimethylethyl ester. The product was purified by silica gel chromatography eluted with 10% acetone in hexane. MS m/z 560 (MH+).

EXAMPLE 52

N-(3-Fluorophenyl)-N-methyl-3-[3-methoxyphenyl (endo-8-azabicyclo[3.2.1]octan-3-yl)amino] benzamide A sample of 3-[[3-[[(3-Fluorophenyl)methylamino] carbonyl]phenyl](3-methoxyphenyl)amino]-endo-8-azabicyclo[3.2.1]octane-8-carboxylic acid 1,1-dimethylethyl ester obtained in Procedure D (1.25 g, 2.23 mmol) was dissolved in 50 mL dichloromethane then 10 mL trifluoroacetic acid was added. The reaction mixture was allowed to stir at about rt for about 30 min and was then poured into a slurry of 200 mL ice and 200 mL 3N NaOH. The organic phase was separated in a separatory funnel then washed with brine, dried over $K_2CO_3$, filtered and concentrated. The title compound was recovered as a pure, clear oil (1.0 g, 100% yield). MS m/z 460 (MH+).

EXAMPLE 53

N-(3-Fluorophenyl)-N-methyl-3-[3-methoxyphenyl (endo-8-allyl-8-azabicyclo[3.2.1]octan-3-yl)amino] benzamide Following the procedure of Example 10 and substituting N-(3-fluorophenyl)-N-methyl-3-[3-methoxyphenyl(endo-8-azabicyclo[3.2.1]octan-3-yl)amino]benzamide for N,N-diethyl-4-[phenyl(endo-8-azabicyclo[3.2.1]octan-3-yl) amino]benzamide, the product N-(3-fluorophenyl)-N-methyl-3-[3-methoxyphenyl(endo-8-allyl-8-azabicyclo [3.2.1]octan-3-yl)amino]benzamide was obtained. MS m/z 500 (MH+).

EXAMPLE 54

N-(3-Fluorophenyl)-N-methyl-3-[3-hydroxyphenyl (endo-8-allyl-8-azabicyclo[3.2.1]octan-3-yl)amino] benzamide To a flask containing 5 mL dry dichloromethane under argon cooled on a dry-ice acetone bath was added N-(3-fluorophenyl)-N-methyl-3-[3-methoxyphenyl(endo-8-allyl-8-azabicyclo[3.2.1]octan-3-yl)amino]benzamide (0.150 g, 0.3 mmol) and 1.5 mL of a 1M boron tribromide solution in dichloromethane (1.5 mmol). The reaction was allowed to warm to rt and was stirred overnight. The reaction was quenched with 50 mL of a saturated $NaHCO_3$ solution and transferred to a separatory funnel. The organic fraction was separated, washed with brine, dried over $K_2CO_3$ and concentrated. The remaining brown oil was then suspended in 100 mL of a saturated $NaHCO_3$ solution and stirred while heating on a steam bath for about 3 h. The product was extracted into dichloromethane, washed with brine, dried over $K_2CO_3$ and concentrated. The remaining brown oil was purified on a Gilson automated reverse-phase HPLC equipped with a $C_{18}$ column eluted with a 30:70:0.1 to 90:10:0.1 gradient ratio of $CH_3CN:H_2O:TFA$ to give the product as the trifluoroacetate salt (50 mg, 33%yield). MS m/z 486 (MH+). $^1$H NMR ($CD_3CN$) δ 7.15–7.3 (m, 4H), 7.0–7.1 (t, 2H), 6.85–6.95 (d, 3H), 6.6–6.65 (t, 1H), 6.5–6.55 (t, 2H), 5.85–6.0 (m, 1H), 5.4–5.5 (d, 2H), 4.05–4.1 (m, 1H), 3.6–3.7 (m, 2H), 3.45–3.5 (t, 2H), 3.40 (s, 3H), 2.2–2.4 (m, 4H), 2.0–2.15 (m, 2H), 1.7–1.85 (d, 2H).

Biological Examples

Delta-opioid and mu-opioid receptor binding for the compounds of the present invention were determined according to the following procedures.

Screening Assay for Delta- and Mu-Opioid Receptor Binding

Rat Brain Delta-Opioid Receptor Binding Assay

Procedure

Male, Wistar rats (150–250 g, VAF, Charles River, Kingston, N.Y.) are killed by cervical dislocation, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is resuspended in the same volume of Tris buffer with several brief pulses from a Polytron homogenizer. This particulate preparation is used for the δ-opioid binding assays. Following incubation with the δ-selective peptide ligand [$^3$H]DPDPE at 25° C., the tube contents are filtered through Whatman GF/B filter sheets on a Brandel cell harvester. The tubes and filters are rinsed three times with 4 mL of 10 mM HEPES (pH 7.4), and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a $K_i$ value (when a range of concentrations is tested).

% Inhibition is calculated as:

$$1 - \left[\frac{(\text{test compound dpm} - \text{nonspecific dpm})}{(\text{total dpm} - \text{nonspecific dpm})}\right] \times 100\%$$

$K_i$ values are calculated using the LIGAND (Munson, P. J. and Rodbard, D., Anal. Biochem. 107: 220–239, 1980) data analysis program.

Rat Brain Mu-Opioid Receptor Binding Assay

Procedure

Male, Wistar rats (150–250 g, VAF, Charles River, Kingston, N.Y.) are killed by cervical dislocation and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is resuspended in the same volume of Tris buffer with several brief pulses from a Polytron homogenizer. This particulate preparation is used for the μ-opioid binding assays. Following incubation with the m-selective peptide ligand [$^3$H]DAMGO at 25° C., the tube contents are filtered through Whatman GF/B filter sheets on a Brandel cell harvester. The tubes and filters are rinsed three times with 4 mL of 10 mM HEPES (pH 7.4) and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a $K_i$ value (when a range of concentrations is tested).

% Inhibition is calculated as:

$$1 - \left[\frac{(\text{test compound dpm} - \text{nonspecific dpm})}{(\text{total dpm} - \text{nonspecific dpm})}\right] \times 100\%$$

$K_i$ values are calculated using the LIGAND (Munson, P. J. and Rodbard, D., Anal. Biochem. 107: 220–239, 1980) data analysis program.

Mouse Acetylcholine Bromide-induced Abdominal Constriction Assay

The activity of compounds of the invention as analgesics may be demonstrated by the mouse acetylcholine-bromide induced constriction assay as described below.

Procedure

The mouse acetylcholine-induced abdominal constriction assay, as described by Collier et al. in Brit. J. Pharmacol. Chem. Ther., 32: 295–310, 1968 with minor modifications, was used to assess analgesic potency of the compounds of Formula (I). The test drugs or appropriate vehicles were administered orally (p.o.) and 30 min later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten min observation period for the occurrence of an abdominal constriction response (defined as a wave of constriction and elongation passing caudally along the abdominal wall, accompanied by a twisting of the trunk and followed by extension of the hind limbs).

As shown in Table 2 for the compounds of the present invention, the percent inhibition of this response to a nociceptive stimulus (equated to % analgesia) was calculated as follows:

% Inhibition of response (i.e., % analgesia) =

$$\frac{(\text{No. of control animal responses} - \text{No. of drug-treated animal responses})}{\text{No. of control animals responding}} \times 100.$$

As a result of this procedure, the compound of Example 7 gave a 60% inhibition response at a dose of about 30 μmole/Kg p.o.

TABLE 2

| Ex # | Delta K, nM | Ex # | Delta K, nM |
|---|---|---|---|
| 1 | 6.59 | 27 | 61 |
| 2 | 20.6 | 28 | 2260 |
| 3 | 8.9 | 29 | 363 |
| 4 | 33.6 | 30 | 53 |
| 5 | 0.36 | 31 | 34 |
| 6 | 8 | 32 | 18 |
| 7 | 3 | 33 | 2 |
| 8 | 2 | 34 | 10 |
| 9 | 0.20 | 35 | 8 |
| 10 | 0.5 | 36 | 6 |
| 11 | 305 | 37 | 18 |
| 12 | 131 | 38 | 459 |
| 13 | 19 | 40 | 6720 |
| 15 | 33 | 41 | 10000 |
| 16 | 151 | 42 | 356 |
| 17 | 72 | 43 | 30 |
| 18 | 550 | 44 | 5 |

TABLE 2-continued

| Ex # | Delta K, nM | Ex # | Delta K, nM |
|---|---|---|---|
| 19 | 77 | 45 | 5 |
| 20 | 42 | 46 | 4 |
| 21 | 6 | 47 | 4 |
| 22 | 4 | 48 | 4 |
| 23 | 12 | 49 | 2 |
| 24 | 9 | 50 | 93 |
| 25 | 24 | 52 | 24.3 |
| 26 | 4 | 53 | 42.6 |
|  |  | 54 | 1.0 |

While the foregoing specification teaches the principles of the present invention, with examples provided for the purpose of illustration, it will be understood that the practice of the invention encompasses all of the usual variation, adaptations and/or modifications as come within the scope of the following claims and their equivalents.

What is claimed is:

1. A compound of Formula (I):

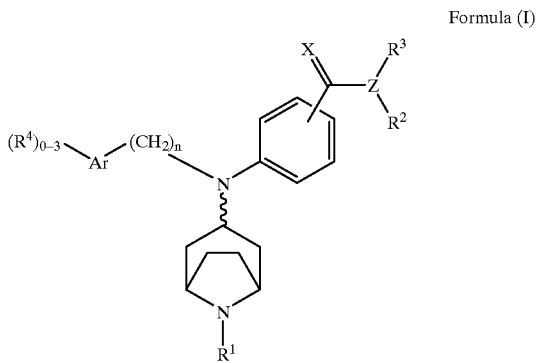

Formula (I)

wherein:

$R^1$ is a substituent selected from the group consisting of hydrogen, $(C_{1-8})$alkyl, $(C_{2-6})$alkenyl, $(C_{3-7})$cycloalkyl, $(C_{3-6})$cycloalkyl$(C_{1-3})$alkyl, $(C_{1-6})$alkoxy$(C_{1-3})$alkyl, 4-$(C_{1-4})$alkyl-4,5-dihydro-5-oxo-1H-tetrazol-1-yl$(C_{1-4})$alkyl, 2-thienyl$(C_{1-4})$alkyl, 3-thienyl$(C_{1-4})$alkyl, 2-furanyl$(C_{1-4})$alkyl, 3-furanyl$(C_{1-4})$alkyl, 2-pyrrolyl$(C_{1-4})$alkyl, 3-pyrrolyl$(C_{1-4})$alkyl, 2-pyridinyl$(C_{1-4})$alkyl, 3-pyridinyl$(C_{1-4})$alkyl, 4-pyridinyl$(C_{1-4})$alkyl, 3-pyrazolyl$(C_{1-4})$alkyl, 4-pyrazolyl$(C_{1-4})$alkyl, 5-pyrazolyl$(C_{1-4})$alkyl, 2-pyrimidinyl$(C_{1-4})$alkyl, 4-pyrimidinyl$(C_{1-4})$alkyl, 5-pyrimidinyl$(C_{1-4})$alkyl, 6-pyrimidinyl$(C_{1-4})$alkyl, 2-thiazolyl$(C_{1-4})$alkyl, 4-thiazolyl$(C_{1-4})$alkyl, 5-thiazolyl$(C_{1-4})$alkyl, 2-oxazolyl$(C_{1-4})$alkyl, 4-oxazolyl$(C_{1-4})$alkyl, 5-oxazolyl$(C_{1-4})$alkyl, phenyl$(C_{1-4})$alkyl and phenyl$(C_{2-4})$alkenyl; wherein the foregoing thienyl, furanyl, pyrrolyl, thiazolyl, oxazolyl, pyrazolyl, pyridinyl, pyrimidinyl and phenyl substituents are optionally substituted with one to three substituents independently selected from the group consisting of hydroxy, halogen, $(C_{1-3})$alkyl, $(C_{2-3})$alkenyl, $(C_{1-3})$alkoxy, $(C_{1-3})$acyl, $(C_{1-10})$acyloxy, cyano, amino, $(C_{1-3})$acylamino, $(C_{1-3})$alkylamino, di$(C_{1-3})$alkylamino, $(C_{1-3})$alkylthio, $(C_{1-3})$alkylsulfonyl, —$OCH_2O$—, —$O(CH_2)_2O$—, trifluoromethyl and trifluoromethoxy;

$R^2$ and $R^3$ are independently selected from the group consisting of hydrogen, $(C_{1-8})$alkyl (optionally substituted with one to three halogen substituents), $(C_{2-6})$alkenyl, $(C_{3-7})$cycloalkyl, phenyl (wherein phenyl is optionally substituted with one to three substituents independently selected from the group consisting of halogen, $(C_{1-6})$alkyl, $(C_{2-6})$alkenyl, $(C_{3-7})$cycloalkyl, —$OCH_2O$—, —$O(CH_2)_2O$— and trifluoromethyl), benzyl (wherein benzyl is optionally substituted with one to three substituents independently selected from the group consisting of halogen, $(C_{1-6})$alkyl, $(C_{2-6})$alkenyl, $(C_{1-6})$alkoxy, $(C_{3-7})$cycloalkyl, —$OCH_2O$—, —$O(CH_2)_2O$— and trifluoromethyl), hydroxy$(C_{1-4})$alkyl, $(C_{1-6})$alkoxy$(C_{1-4})$alkyl and trifluoro$(C_{1-4})$alkoxy; alternatively, $R^2$ and $R^3$ may form a single fused moiety selected from the group consisting of 1,4-butylene, 1,5-pentylene, 1,5-(3-oxapentylene) and 1,5-(3-azapentylene); wherein the moiety is optionally substituted with one to four substituents independently selected from the group consisting of $(C_{1-6})$alkyl, $(C_{2-6})$alkenyl and $(C_{3-7})$cycloalkyl;

the moiety —C(=X)Z is substituted on phenyl at the 3 or 4 position; wherein X is selected from the group consisting of S and O; Z is selected from the group consisting of N and O; and, Z is optionally substituted with one to two substituents independently selected from the group consisting of $R^2$ and $R^3$;

with the proviso that:
if Z is O, then Z is optionally substituted with one substituent selected from $R^2$;

n is selected from 0 or 1;

Ar is selected from the group consisting of phenyl, 1-naphthyl and 2-naphthyl; wherein Ar is optionally substituted with from one to three substituents independently selected from $R^4$; and, $R^4$ is independently selected from the group consisting of hydroxy, halogen, $(C_{1-3})$alkyl, $(C_{2-3})$alkenyl, $(C_{1-3})$alkoxy, $(C_{1-3})$acyl, $(C_{1-10})$acyloxy, cyano, amino, $(C_{1-3})$acylamino, $(C_{1-3})$alkylamino, di$(C_{1-3})$alkylamino, $(C_{1-3})$alkylthio, $(C_{1-3})$alkylsulfonyl, —$OCH_2O$—, —$O(CH_2)_2O$—, trifluorcimethyl and trifluoromethoxy; and, alternatively, two adjacent $R^4$ groups may form a single fused moiety, wherein the moiety is selected from the group consisting of —$(CH_2)_{3-5}$— and —$O(CH_2)_{1-3}O$—;

and pharmaceutically acceptable diastereomers and salts thereof.

2. The compound of claim 1 wherein $R^1$ is selected from the group consisting of hydrogen, methyl, ethyl, n-propyl, n-butyl, 2-ethyl-n-butyl, n-hexyl, cyclopropylmethyl, cyclohexylmethyl, cyclohexyl, allyl, 3,3-dimethylallyl, 2-methylpropenyl, piperonyl, phenethyl, 4-fluorophenethyl, 3,4-dimethoxyphenethyl, diphenylethyl, phenylpropyl, 2-thienylethyl and 2-furanylmethyl.

3. The compound of claim 1 wherein $R^1$ is selected from the group consisting of hydrogen, methyl, n-propyl, allyl, piperonyl, 3,4-dimethoxyphenethyl, phenylpropyl and 2-furanylmethyl.

4. The compound of claim 1 wherein $R^1$ is selected from the group consisting of hydrogen, allyl and piperonyl.

5. The compound of claim 1 wherein $R^2$ and $R^3$ are independently selected from the group consisting of methyl, ethyl, 2-fluoroethyl, n-propyl, isopropyl, n-butyl, t-butyl, 2-methylallyl, phenyl, 3-fluorophenyl and 4-methylbenzyl; and, alternatively, $R^2$ and $R^3$ may form a single fused moiety selected from 1,4-butylene.

6. The compound of claim 1 wherein $R^2$ and $R^3$ are independently selected from the group consisting of methyl, ethyl, 2-fluoroethyl, n-propyl, n-butyl, 2-methylallyl, phenyl and 3-fluorophenyl.

7. The compound of claim 1 wherein $R^2$ and $R^3$ are independently selected from ethyl.

8. The compound of claim 1 wherein n is 0.

9. The compound of claim 1 wherein Ar is phenyl.

10. The compound of claim 1 wherein $R^4$ is independently selected from the group consisting of hydroxy, chloro, bromo, fluoro, methyl, ethyl, methoxy, ethoxy, methylamino, N,N-dimethylamino, methylthio, methylsulfonyl, trifluoromethoxy and trifluoromethyl.

11. The compound of claim 1 wherein $R^4$ is independently selected from the group consisting of hydroxy, methoxy and methylthio.

12. The compound of claim 1 wherein $R^4$ is not present.

13. The compound of claim 1 having the structure:

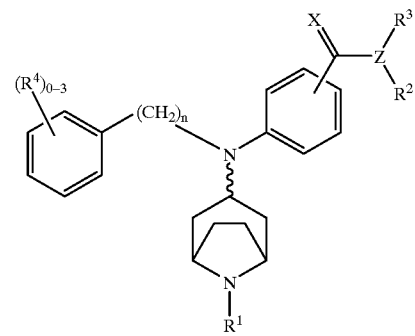

wherein $R^1$, $-C(=X)Z$, $R^2$, $R^3$, n and $R^4$ are dependently selected from the group consisting of:

| Isomer | $R^1$ | $-C(=X)Z$ | $R^2$ | $R^3$ | n | $R^4$ |
|---|---|---|---|---|---|---|
| endo | $CH_3$ | 4-C(=O)N | $CH_2CH_3$ | $CH_2CH_3$ | 0 | ---; |
| endo | $CH_3$ | 4-C(=O)N | $CH_2CH_3$ | $CH_2CH_3$ | 0 | 3-$OCH_3$; |
| endo | $CH_3$ | 4-C(=O)N | $CH_2CH_3$ | $CH_2CH_3$ | 0 | 3-$SCH_3$; |
| endo | $CH_3$ | 4-C(=O)N | $CH_2CH_3$ | $CH_2CH_3$ | 1 | ---; |
| endo | H | 4-C(=O)N | $CH_2CH_3$ | $CH_2CH_3$ | 0 | ---; |
| endo | $(CH_2)_2Ph$ | 4-C(=O)N | $CH_2CH_3$ | $CH_2CH_3$ | 0 | ---; |
| endo | $(CH_2)_2CH_3$ | 4-C(=O)N | $CH_2CH_3$ | $CH_2CH_3$ | 0 | ---; |
| endo | $C_6H_{11}$ | 4-C(=O)N | $CH_2CH_3$ | $CH_2CH_3$ | 0 | ---; |
| endo | piperonyl | 4-C(=O)N | $CH_2CH_3$ | $CH_2CH_3$ | 0 | ---; |
| endo | $CH_2CH=CH_2$ | 4-C(=O)N | $CH_2CH_3$ | $CH_2CH_3$ | 0 | ---; |
| exo | $CH_3$ | 4-C(=O)N | $CH_2CH_3$ | $CH_2CH_3$ | 0 | ---; |
| exo | $CH_3$ | 4-C(=O)N | $(CH_2)_2CH_3$ | $(CH_2)_2CH_3$ | 0 | ---; |
| exo | H | 4-C(=O)N | $CH_2CH_3$ | $CH_2CH_3$ | 0 | ---; |
| exo | $CH_3$ | 4-C(=O)N | H | $(CH_2)_2CH_3$ | 0 | ---; |
| exo | $(CH_2)_5CH_3$ | 4-C(=O)N | $CH_2CH_3$ | $CH_2CH_3$ | 0 | ---; |
| exo | $(CH_2)_2CH_3$ | 4-C(=O)N | $CH_2CH_3$ | $CH_2CH_3$ | 0 | ---; |
| exo | $(CH_2)_2Ph$ | 4-C(=O)N | $CH_2CH_3$ | $CH_2CH_3$ | 0 | ---; |
| exo | $CH_2CH(Ph)_2$ | 4-C(=O)N | $CH_2CH_3$ | $CH_2CH_3$ | 0 | ---; |
| exo | $CH_2C_6H_{11}$ | 4-C(=O)N | $CH_2CH_3$ | $CH_2CH_3$ | 0 | ---; |
| exo | $CH_2CH(CH_2CH_3)_2$ | 4-C(=O)N | $CH_2CH_3$ | $CH_2CH_3$ | 0 | ---; |
| exo | 2-furanyl$CH_2$ | 4-C(=O)N | $CH_2CH_3$ | $CH_2CH_3$ | 0 | ---; |
| exo | piperonyl | 4-C(=O)N | $CH_2CH_3$ | $CH_2CH_3$ | 0 | ---; |
| exo | $CH_2CH=C(CH_3)_2$ | 4-C(=O)N | $CH_2CH_3$ | $CH_2CH_3$ | 0 | ---; |
| exo | $(CH_2)_2$-3,4-$(CH_3O)_2Ph$ | 4-C(=O)N | $CH_2CH_3$ | $CH_2CH_3$ | 0 | ---; |
| exo | $(CH_2)_2$4-F-Ph | 4-C(=O)N | $CH_2CH_3$ | $CH_2CH_3$ | 0 | ---; |
| exo | $(CH_2)_3Ph$ | 4-C(=O)N | $CH_2CH_3$ | $CH_2CH_3$ | 0 | ---; |
| exo | $(CH_2)_2Ph$ | 4-C(=O)N | $(CH_2)_2CH_3$ | $(CH_2)_2CH_3$ | 0 | ---; |
| endo | $CH_3$ | 4-C(=O)O | $C(CH_3)_3$ | — | 0 | ---; |
| endo | $CH_3$ | 4-C(=O)O | — | — | 0 | ---; |
| endo | $CH_3$ | 4-C(=O)N | $CH_3$ | $CH_3$ | 0 | ---; |
| endo | $CH_3$ | 4-C(=O)N | —$(CH_2)_4$— | | 0 | ---; |
| endo | $CH_3$ | 4-C(=O)N | $CH_3$ | $CH_2CH_3$ | 0 | ---; |
| endo | $CH_3$ | 4-C(=O)N | $CH_2CH_3$ | $CH_2C(CH_3)=CH_2$ | 0 | ---; |
| endo | $CH_3$ | 4-C(=O)N | $CH_2CH_3$ | $CH_2(4-CH_3Ph)$ | 0 | ---; |
| endo | $CH_3$ | 4-C(=O)N | $(CH_2)_2CH_3$ | $(CH_2)_3CH_3$ | 0 | ---; |
| endo | $CH_3$ | 4-C(=O)N | $CH_3$ | Ph | 0 | ---; |
| endo | $CH_3$ | 4-C(=O)N | $(CH_2)_2CH_3$ | $(CH_2)_2CH_3$ | 0 | ---; |
| endo | $CH_3$ | 3-C(=O)O | $C(CH_3)_3$ | — | 0 | ---; |
| endo | $CH_3$ | 4-C(=O)N | — | H | 0 | ---; |
| endo | $CH_3$ | 3-C(=O)N | $CH_2CH_3$ | $CH_2CH_3$ | 0 | ---; |
| endo | $(CH_2)_2Ph$ | 4-C(=O)O | $C(CH_3)_3$ | — | 0 | ---; |
| endo | $(CH_2)_2Ph$ | 4-C(=O)O | — | — | 0 | ---; |
| endo | $(CH_2)_2Ph$ | 4-C(=O)N | $CH_3$ | $CH_3$ | 0 | ---; |
| endo | $(CH_2)_2Ph$ | 4-C(=O)N | $CH_3$ | $CH_2CH_3$ | 0 | ---; |
| endo | $(CH_2)_2Ph$ | 4-C(=O)N | $CH_2CH_3$ | $(CH_2)_3CH_3$ | 0 | ---; |
| endo | $(CH_2)_2Ph$ | 4-C(=O)N | $(CH_2)_2CH_3$ | $(CH_2)_2CH_3$ | 0 | ---; |
| endo | $(CH_2)_2Ph$ | 4-C(=O)N | $CH_3$ | $(CH_2)_2CH_3$ | 0 | ---; |
| endo | $(CH_2)_2Ph$ | 4-C(=O)N | $CH_3$ | $(CH_2)_3CH_3$ | 0 | ---; |
| endo | $(CH_2)_2Ph$ | 4-C(=O)N | $CH_2CH_3$ | $CH_2C(CH_3)=CH_2$ | 0 | ---; |
| endo | $(CH_2)_2Ph$ | 4-C(=O)N | —$(CH_2)_4$— | | 0 | ---; |
| endo | $CH_3$ | 4-C(=S)N | $CH_2CH_3$ | $CH_2CH_3$ | 0 | ---; |
| endo | H | 3-C(=O)N | $CH_3$ | 3-F-Ph | 0 | 3-$OCH_3$; |

| Isomer | $R^1$ | —C(=X)Z | $R^2$ | $R^3$ | n | $R^4$ |
|---|---|---|---|---|---|---|
| endo and, | $CH_2CH=CH_2$ | 3-C(=O)N | $CH_3$ | 3-F-Ph | 0 | 3-$OCH_3$; |
| endo | $CH_2CH=CH_2$ | 3-C(=O)N | $CH_3$ | 3-F-Ph | 0 | 3-OH; | and pharmaceutically acceptable diastereomers and salts thereof.

14. The compound of claim 1 having the structure:

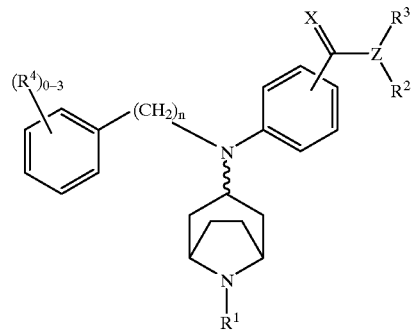

wherein $R^1$, —C(=X)Z, $R^2$, $R^3$, n and $R^4$ are dependently selected from the group consisting of:

and pharmaceutically acceptable diastereomers and salts thereof.

15. The compound of claim 1 having the structure:

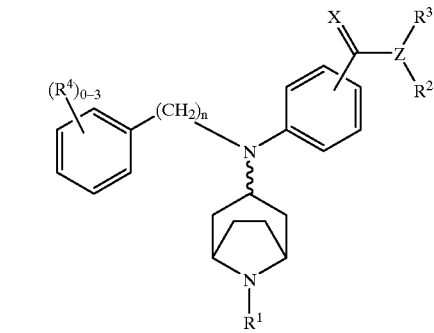

wherein $R^1$, —C(=X)Z, $R^2$, $R^3$, n and $R^4$ are dependently selected from the group consisting of:

| Isomer | $R^1$ | —C(=X)Z | $R^2$ | $R^3$ | n | $R^4$ |
|---|---|---|---|---|---|---|
| endo | $CH_3$ | 4-C(=O)N | $CH_2CH_3$ | $CH_2CH_3$ | 0 | ---; |
| endo | $CH_3$ | 4-C(=O)N | $CH_2CH_3$ | $CH_2CH_3$ | 0 | 3-$SCH_3$; |
| endo | H | 4-C(=O)N | $CH_2CH_3$ | $CH_2CH_3$ | 0 | ---; |
| endo | $(CH_2)_2Ph$ | 4-C(=O)N | $CH_2CH_3$ | $CH_2CH_3$ | 0 | ---; |
| endo | $(CH_2)_2CH_3$ | 4-C(=O)N | $CH_2CH_3$ | $CH_2CH_3$ | 0 | ---; |
| endo | $C_6H_{11}$ | 4-C(=O)N | $CH_2CH_3$ | $CH_2CH_3$ | 0 | ---; |
| endo | piperonyl | 4-C(=O)N | $CH_2CH_3$ | $CH_2CH_3$ | 0 | ---; |
| endo | $CH_2CH=CH_2$ | 4-C(=O)N | $CH_2CH_3$ | $CH_2CH_3$ | 0 | ---; |
| exo | $(CH_2)_2Ph$ | 4-C(=O)N | $CH_2CH_3$ | $CH_2CH_3$ | 0 | ---; |
| exo | 2-furanyl$CH_2$ | 4-C(=O)N | $CH_2CH_3$ | $CH_2CH_3$ | 0 | ---; |
| exo | piperonyl | 4-C(=O)N | $CH_2CH_3$ | $CH_2CH_3$ | 0 | ---; |
| exo | $(CH_2)_2$-3,4-$(CH_3O)_2Ph$ | 4-C(=O)N | $CH_2CH_3$ | $CH_2CH_3$ | 0 | ---; |
| exo | $(CH_2)_2$4-F-Ph | 4-C(=O)N | $CH_2CH_3$ | $CH_2CH_3$ | 0 | ---; |
| exo | $(CH_2)_3Ph$ | 4-C(=O)N | $CH_2CH_3$ | $CH_2CH_3$ | 0 | ---; |
| exo | $(CH_2)_2Ph$ | 4-C(=O)N | $(CH_2)_2CH_3$ | $(CH_2)_2CH_3$ | 0 | ---; |
| endo | $CH_3$ | 4-C(=O)N | $CH_2CH_3$ | $CH_2C(CH_3)=CH_2$ | 0 | ---; |
| endo | $CH_3$ | 4-C(=O)N | $(CH_2)_2CH_3$ | $(CH_2)_3CH_3$ | 0 | ---; |
| endo | $CH_3$ | 4-C(=O)N | $CH_3$ | Ph | 0 | ---; |
| endo | $(CH_2)_2Ph$ | 4-C(=O)N | $CH_3$ | $CH_3$ | 0 | ---; |
| endo | $(CH_2)_2Ph$ | 4-C(=O)N | $CH_3$ | $CH_2CH_3$ | 0 | ---; |
| endo | $(CH_2)_2Ph$ | 4-C(=O)N | $CH_2CH_3$ | $(CH_2)_3CH_3$ | 0 | ---; |
| endo | $(CH_2)_2Ph$ | 4-C(=O)N | $(CH_2)_2CH_3$ | $(CH_2)_2CH_3$ | 0 | ---, |
| endo | $(CH_2)_2Ph$ | 4-C(=O)N | $CH_3$ | $(CH_2)_2CH_3$ | 0 | ---; |
| endo | $(CH_2)_2Ph$ | 4-C(=O)N | $CH_3$ | $(CH_2)_3CH_3$ | 0 | ---; |
| endo | $(CH_2)_2Ph$ | 4-C(=O)N | $CH_2CH_3$ | $CH_2C(CH_3)=CH_2$ | 0 | ---; |
| endo | $(CH_2)_2Ph$ | 4-C(=O)N | —$(CH_2)_4$— | | 0 | ---; |
| endo | H | 3-C(=O)N | $CH_3$ | 3-F-Ph | 0 | 3-$OCH_3$; |
| endo | $CH_2CH=CH_2$ | 3-C(=O)N | $CH_3$ | 3-F-Ph | 0 | 3-$OCH_3$; |
| endo and, | $CH_2CH=CH_2$ | 3-C(=O)N | $CH_3$ | 3-F-Ph | 0 | 3-OH; |

| Isomer | R¹ | —C(=X)Z | R² | R³ | n | R⁴ |
|---|---|---|---|---|---|---|
| endo | H | 4-C(=O)N | CH₂CH₃ | CH₂CH₃ | 0 | ---; |
| endo and, | piperonyl | 4-C(=O)N | CH₂CH₃ | CH₂CH₃ | 0 | ---; |
| endo | CH₂CH=CH₂ | 4-C(=O)N | CH₂CH₃ | CH₂CH₃ | 0 | ---; | and pharmaceutically acceptable diastereomers and salts thereof.

16. The compound of claim 1 which is an effective delta-opioid receptor modulator.

17. The compound of claim 1 which is an effective delta-opioid receptor agonist.

18. The compound of claim 1 which is an effective analgesic.

19. The compound of claim 1 which is an effective delta-opioid receptor antagonist.

20. The compound of claim 1 which is an effective immunosuppressant, antiinflammatory agent, agent for the treatment of neurological and psychiatric conditions, medicament for drug and alcohol abuse, agent for treating gastritis and diarrhea, cardiovascular agent or agent for the treatment of respiratory diseases.

21. A pharmaceutical composition comprising a compound of claim 1 and a pharmaceutically acceptable carrier.

22. A pharmaceutical composition made by mixing a compound of claim 1 and a pharmaceutically acceptable carrier.

23. A pharmaceutical composition comprising a combination of the compound of claim 1 and a compound effective as a mu-opioid modulator.

24. The pharmaceutical composition of claim 20 wherein the compound effective as a mu-opioid modulator is selected from the group consisting of alfentanil, allylprodine, alphaprodine, anileridine, benzyl-morphine, bezitramide, buprenorphine, butorphanol, clorlitazene, cyclazocine, desomorphine, dextromoramide, dezocine, diampromide, diamorphone, dihydrocodeine, dihydromorphine, dimenoxadol, dimepheptanol dimethylthiambutene, dioxaphetylbutyrate, dipipanone, eptazocine, ethoheptazine, ethylmethylthiambutene, ethylmorphine, etonitazene fentanyl, heroin, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norievorphanol, normethadone, nalorphine, riormorphine, norpipanone, opium, oxycodone, oxymorphone, papaveretum, pentazocine, phenadoxone, phenomorphan, phenazocine, phenoperidine, piminodine, piritramide, propheptazine, promeadol, properidine, propiram, propoxyphene, sufentanil, tilidine, tramadol, salts thereof, complexes thereof; and mixtures of any of the foregoing.

25. A method for treating a disorder modulated by the delta-opioid receptor in a subject in need thereof comprising administering to the subject a therapeutically effective amount of a compound of claim 1.

26. The method of claim 22 wherein the therapeutically effective amount of the compound of claim 1 is from about 0.01 mg/day to about 12,000 mg/day.

27. The method of claim 22 wherein the disorder is pain modulated by a therapeutically effective amount of a compound of claim 1.

28. The method of claim 22 wherein the disorder is selected from the group consisting of immune disorders, inflammation, neurological conditions, psychiatric conditions, drug abuse, alcohol abuse, gastritis, diarrhea, cardiovascular disorders and respiratory disorders modulated by a therapeutically effective amount of a compound of claim 1.

29. The method of claim 22 further comprising administering to the subject a therapeutically effective amount of a pharmaceutical composition of claim 18.

30. The method of claim 26 wherein the therapeutically effective amount of the pharmaceutical composition of claim 18 is from about 0.01 mg/day to about 12,000 mg/day.

* * * * *